(12) United States Patent
Decout et al.

(10) Patent No.: US 8,729,035 B2
(45) Date of Patent: May 20, 2014

(54) SYNTHESIS OF NOVEL NEAMINE DERIVATIVES AND USE THEREOF AS ANTIBACTERIAL AGENTS

(75) Inventors: Jean-Luc Decout, St. Martin d'uriage (FR); Isabelle Baussanne, Lans en Vercors (FR); Jerome Desire, Tencin (FR); Jean-Marc Paris, Vaires sur Marne (FR)

(73) Assignee: Universite Joseph Fourier, Grenoble Cedex (FR)

( * ) Notice: Subject to any disclaimer, the term of this patent is extended or adjusted under 35 U.S.C. 154(b) by 257 days.

(21) Appl. No.: 12/735,511

(22) PCT Filed: Jan. 22, 2009

(86) PCT No.: PCT/FR2009/050088
§ 371 (c)(1),
(2), (4) Date: Jul. 22, 2010

(87) PCT Pub. No.: WO2009/095588
PCT Pub. Date: Aug. 6, 2009

(65) Prior Publication Data
US 2010/0311680 A1    Dec. 9, 2010

(30) Foreign Application Priority Data

Jan. 22, 2008 (FR) ..................................... 08 50397

(51) Int. Cl.
*A61K 31/70* (2006.01)
*C07H 15/20* (2006.01)
*C07H 15/22* (2006.01)

(52) U.S. Cl.
USPC ........................................... 514/36; 536/16.6

(58) Field of Classification Search
None
See application file for complete search history.

(56) References Cited

U.S. PATENT DOCUMENTS

2006/0234961 A1   10/2006   Chang

FOREIGN PATENT DOCUMENTS

FR          2 913 611       9/2008
WO     WO 2005/060573     7/2005

OTHER PUBLICATIONS

Simonsen et al., ChemBioChem 2002, vol. 3, pp. 1223-1228.*
Ryu et al., Bioorganic and Medicinal Chemistry Letters, 2003, vol. 13, 901-903.*
Jikihara, T. et al.: "Studies on aminosugars. XXXV. Synthesis of 3',4'-dideoxyneamine and 3'- and 4'-0-methylneamines", Bulletin of the Chemical Society of Japan, 1973, pp. 3507-3510, vol. 46.
Nagabhushan, T.L., Daniels, P.J.L.: "Synthesis and biological properties of 6'-amino-6'-deoxygentamicin A", J. Med. Chem, 1974, pp. 1030-1031, vol. 17.

Riguet, E. et al.: "A route for preparing new neamine derivatives targeting HIV-1 TAR RNA", Tetrahedron, 2004, pp. 8053-8064, vol. 60, No. 37, Elsevier Science Publishers, Amsterdam, NL.
Liu, M. et al.: "Tethered bisubstrate derivatives as probes for mechanism and as inhibitors of aminoglycoside 3'-phosphotransferases", J. Org. Chem., 2000, pp. 7422-7431, vol. 65.
Ryu, D.H. et al.: "Synthesis of (+),(−)-Neamine and their positional isomers as potential antibiotics", Bioorganic & Medicinal Chemistry Letters, 2003, pp. 901-903, vol. 13.
Haddad, J. et al.: "Design of novel antibiotics that bind to the ribosomal acyltransfer site", Journal of the American Chemical Society, 2002, pp. 3229-3237, vol. 124, No. 13.
Jiao, G.S. et al.: "Selectively guanidinylated derivatives of neamine. Syntheses and inhibition of anthrax lethal factor protease", Bioorganic & Medicinal Chemistry Letters, 2006, pp. 5183-5189, vol. 16, No. 19, Elsevier Science.
Greenberg, W.A. et al.: "Design and synthesis of new animoglycoside antibiotics containing neamine as an optimal core structure: correlation of antibiotic activity with in vitro inhibition of translation", Journal of the American Chemical Society, 1999, pp. 6527-6541, vol. 121.
Sucheck, S.J. et al.: "Design of small molecules that recognize RNA: development of aminoglycosides as potential antitumor agents that target oncogenic RNA sequences", Angew. Chem. Int., 2000, pp. 1080-1084, vol. 39, No. 6.
Moazed D. et al.: "Interaction of antibiotics with functional sites in 16S ribosomal RNA", Nature, 1987, pp. 389-394, vol. 327, No. 6121 (Abstract Only).
Riguet, E., "A peptide nucleic acid-neamine conjugate that targets and cleaves HIV-1 TAR RNA inhibits viral replication", J. Med. Chem., 2004, pp. 4806-4809, vol. 47, No. 20 (Abstract Only).
Riguet, E., "Neamine dimers targeting the HIV-1 TAR RNA", Bioorganic & Medicinal Chemistry Letters, 2005, pp. 4651-4655, vol. 15, No. 21 (Abstract Only).

* cited by examiner

*Primary Examiner* — Traviss C McIntosh, III
(74) *Attorney, Agent, or Firm* — Wolf, Greenfield & Sacks, P.C.; C. Hunter Baker

(57) ABSTRACT

This invention concerns compounds with the formula:

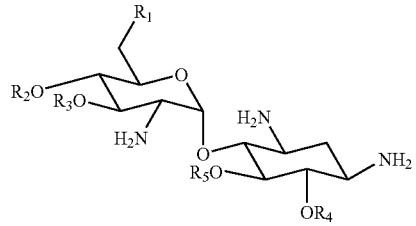

in which:
  $R_1$=OH or $NH_2$;
  $OR_2$, $OR_3$, $OR_4$ and $OR_5$ are alcohol, ether, ester, carbonate, carbamate, sulphonate or sulphamate groups; and
  if $R_5$=H
    if $R_2$=$R_3$=$R_4$, then $R_2$, $R_3$ and $R_4 \neq H$;
    if $R_2$=H, then $R_3 \neq H$ and $R_4 \neq H$;
    if $R_3$=H, then $R_2 \neq H$ and $R_4 \neq H$;
    if $R_4$=H, then $R_2 \neq H$ and $R_3 \neq H$;
  if $R_5 \neq H$
    if R2=H, then $R_3 \neq H$ and $R_4 \neq H$;
    if $R_3$=H, then $R_2 \neq H$ and $R_4 \neq H$;
    if $R_4$=H, then $R_2 \neq H$ and $R_3 \neq H$,
their use as antibiotic agents and the process for synthesizing them.

23 Claims, No Drawings

SYNTHESIS OF NOVEL NEAMINE DERIVATIVES AND USE THEREOF AS ANTIBACTERIAL AGENTS

CROSS REFERENCE TO RELATED APPLICATIONS

This application is a national stage filing under 35 U.S.C. §371 of PCT International application PCT/FR2009/050088 designating the United States of America, filed Jan. 22, 2009, which claims the benefit of French application serial number 0850397, filed Jan. 22, 2008, both of which are incorporated herein by reference.

TECHNICAL FIELD

This invention concerns antibacterial agents.

More precisely, new derivatives of neamine have been synthesised which appear to be very active.

PRIOR ART

The aminoglycosides are natural polyaminated pseudo-polysaccharides synthesised by Gram positive bacteria to combat other bacteria. The first compounds of this family were discovered in the 1940s and were identified as potent antibiotic agents which were very quickly used in hospitals. Streptomycin, neomycin, kanamycin and gentamicin were the first molecules of the aminoglycoside family to be isolated.

The majority of aminoglycosides have as a common structural element a streptamine or 2-deoxystreptamine ring joined, by a glycosidic bond, to one or two mono- or disaccharide units. These include (shown below) paromamine (1) and neamine (2), composed of ring I (2-deoxystreptamine) joined at position 4 to ring II by a glycosidic bond. These two compounds form the basic pattern for two large families of aminoglycosides:

the family of derivatives substituted in position 5, to which paromomycin (3) and neomycin (4) belong;

the family of derivatives (5) substituted in position 6, to which kanamycin and tobramycin belong.

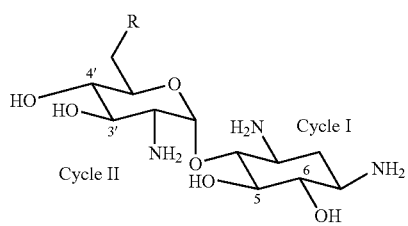

1 : R = OH, Paromamine
2 : R = NH$_2$, Neamine

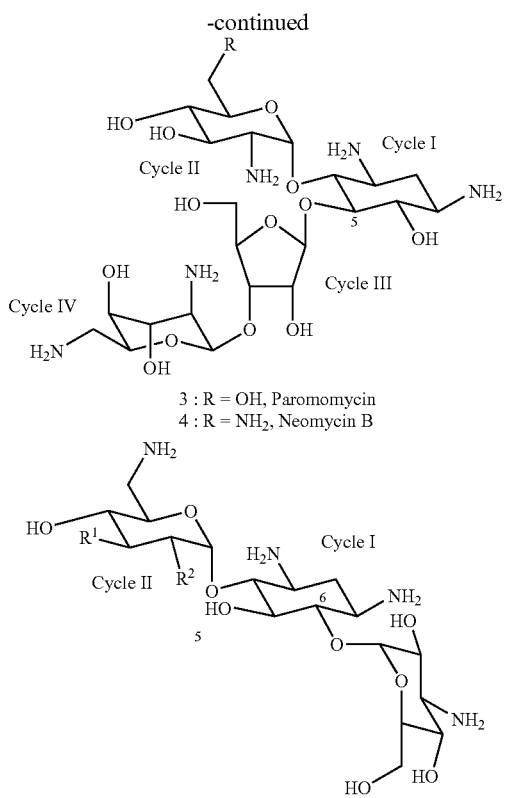

3 : R = OH, Paromomycin
4 : R = NH$_2$, Neomycin B $R^1$ : $R^2$ = OH: Kanamycin
$R^1$ = OH, $R^2$ = NH$_2$ : Kanamycin B
$R^1$ = H, $R^2$ = NH$_2$: Tobramycin Among present antibiotic agents, the aminoglycosides represent a very important class of molecules essentially used in a hospital environment. The restriction of use to this environment minimises the risk of resistant bacteria developing, allowing access to active molecules in emergencies.

Most aminoglycosides have an antibiotic effect against both Gram positive and Gram negative bacteria. They are often administered in combination with β-lactams or fluoroquinolones, to widen their spectra. On the other hand, all the aminoglycosides are inactive on anaerobic bacteria and mycoplasma.

Aminoglycosides have several methods of action, the main one being disrupting protein synthesis by a strong interaction with site A of bacterial 16S ribosomal RNA. In 1987, Mozaed and Noller showed that certain aminoglycosides specifically interact with ribosomal RNA. Since this discovery, other RNAs for which aminoglycosides are good ligands have been identified. They are, for example, capable of fixing onto TAR, RRE and DIS RNA of HIV-1.

Their antibiotic effects are also due to the modifications which they induce to the properties of the bacterial membrane.

Unfortunately, aminoglycosides have some drawbacks when they are used as medicinal products. Indeed, their toxicity limits their therapeutic use, and, as for many other agents, resistance has appeared. Resistant bacterial strains are thus responsible for nosocomial diseases, which are a major health problem.

These resistant forms involve enzymatic modifications to the structure of the aminoglycosides that make them incapable of binding to bacterial ribosomal RNA, reduction of their intracellular concentration by efflux, alteration to the structure of the 30S sub-unit of the target RNA and methylation of the aminoglycoside binding site in the RNA.

As regards resistance caused by the modification enzymes synthesised by certain bacteria, there are three classes of resistance enzymes:

- aminoglycoside O-phosphotransferases (APH) and aminoglycoside nucleotidyltransferases (ANT) which phosphorylate the hydroxyl groups of aminoglycosides using ATP;
- aminoglycoside N-acetyltransferases (AAC) which catalyse acylation of the amine groups of aminoglycoside using coenzyme A.

The modification enzymes are specific to different aminoglycoside positions. An enzyme which phosphorylates the hydroxyl group at the 3' position on ring II will have the name APH3'. For example, kanamycin B is modified by the following enzymes:

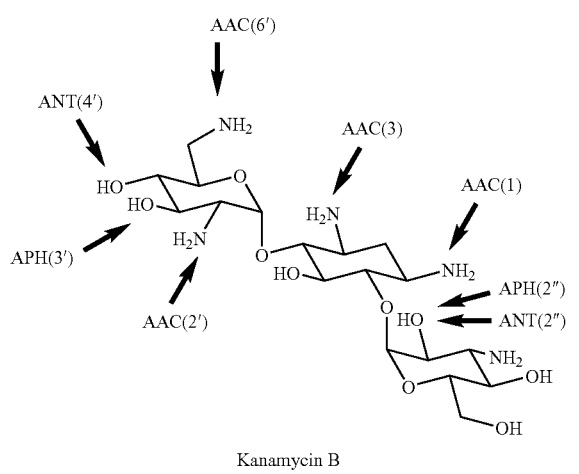

Kanamycin B

NB: A bifunctional enzyme, AAC(6')-APH(2") was discovered in 1997.

As regards the mechanisms that contribute to reducing the cellular concentration of active molecules, efflux pumps in the cell membrane of prokaryote cells form a mechanism rejecting xenobiotic agents that could intoxicate the cell. A mutation can make these pumps over-activated. Some cells have mutations in the genes regulating these pumps so that they are over-expressed and the rejection of xenobiotics is less selective allowing efflux of aminoglycosides (Multi-Drug Resistant or MDR systems).

The major antibiotic effects of the aminoglycosides and the problems of resistance have thus led to renewed interest in the chemistry of these molecules in order to find new antibiotic and/or antiviral agents. In particular this has consisted of identifying new agents acting on bacteria resistant to the currently available aminoglycosides and hence to present treatment.

This invention comes within this area. In fact, the applicant has developed a new aminoglycoside synthetic pathway, particularly for derivatives of neamine or paromamine, and has shown that these derivatives have remarkable antibiotic properties.

DESCRIPTION OF THE INVENTION

Thus, in a first aspect, the invention concerns compounds with the following formula:

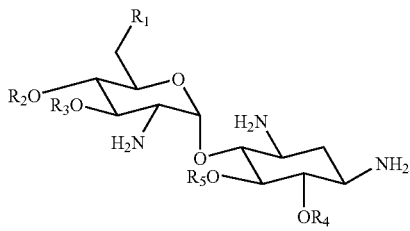

in which:
$R_1$=OH or $NH_2$;
$OR_2$, $OR_3$, $OR_4$ and $OR_5$ are alcohol, ether, ester, carbonate, carbamate, sulphonate or sulphamate groups; and
if $R_5$=H
 if $R_2$=$R_3$=$R_4$, then $R_2$, $R_3$ and $R_4 \neq H$;
 if $R_2$=H, then $R_3 \neq H$ and $R_4 \neq H$;
 if $R_3$=H, then $R_2 \neq H$ and $R_4 \neq H$;
 if $R_4$=H, then $R_2 \neq H$ and $R_3 \neq H$;
if $R_5 \neq H$
 if $R_2$=H, then $R_3 \neq H$ and $R_4 \neq H$;
 if $R_3$=H, then $R_2 \neq H$ and $R_4 \neq H$;
 if $R_4$=H, then $R_2 \neq H$ and $R_3 \neq H$.

According to a preferred embodiment, the formula of the compounds according to the invention is as follows:

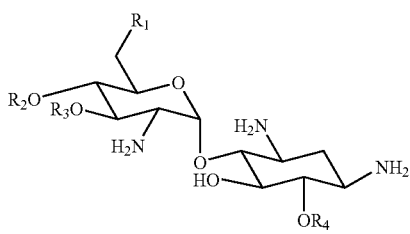

in which:
$R_1$=OH or $NH_2$;
$OR_2$, $OR_3$ and $OR_4$ are alcohol, ether, ester, carbonate, carbamate, sulphonate or sulphamate groups; and
if $R_2$=$R_3$=$R_4$, then $R_2$, $R_3$ and $R_4 \neq H$;
if $R_2$=H, then $R_3 \neq H$ and $R_4 \neq H$;
if $R_3$=H, then $R_2 \neq H$ and $R_4 \neq H$;
if $R_4$=H, then $R_2 \neq H$ and $R_3 \neq H$.

In other words, this invention concerns the derivatives of neamine or paromamine disubstituted (3'+6 or 3'+4' or 4'+6) or trisubstituted (3'+4'+6) in positions 3', 4' and/or 6. Also concerned by this invention are trisubstituted derivatives of neamine or paromamine involving position 5 (3'+6+5 or 3'+4'+5 or 4'+6+5).

In the neamine and paromamine formula, $OR_2$, $OR_3$, $OR_4$ and $OR_5$ are alcohol groups with the formula OH.

According to the invention, at least two or three of these alcohol groups are replaced by ether, ester, carbonate, carbamate, sulphonate or sulphamate groups.

If should be noted that the compounds according to the invention may occur in the form of salts, resulting from the reaction of the amine groups with an acid. Thus, neamine derivatives ($R_1$=$NH_2$) occur in the protonated form e.g. in the form of tetrachlorhydrates or tetratrifluoroacetates.

In the alcohol group, the oxygen has a single bond to a hydrogen atom (OH).

In the ether group, the oxygen has a single bond to a carbon atom, which is itself involved in an alkyl type (OCRR'R") or aryl type (OAr) group.

In the ester group, the oxygen has a single bond to a carbon atom, which itself has a double bond to another oxygen atom (OCOR).

In the carbonate group, the oxygen has a single bond to a carbon atom, which itself has a double bond to a second oxygen atom and another single bond to a third oxygen atom (OC(O)OR).

In the carbamate group, the oxygen has a single bond to a carbon atom, which itself has a double bond to another oxygen atom and a single bond to a nitrogen atom (OC(O)NHR or OC(O)NRR').

In the sulphonate group, the oxygen has a single bond to a sulphur atom, which itself has two double bonds each to an oxygen atom and a single bond to a carbon atom ($OSO_2R$).

In the sulphamate group, the oxygen has a single bond to a sulphur atom, which itself has two double bonds each to an oxygen atom and a single bond to a nitrogen atom ($OSO_2NHR$ or $OSO_2NRR'$).

The nature of these functional groups results from the process used to synthesise these derivatives, as described hereafter.

It can be clearly seen that in the compounds concerned by this invention, the $OR_2$, $OR_3$ and $OR_4$, and possibly $OR_5$ groups may be independently selected from the group formed by the alcohol, ether, ester, carbonate, carbamate, sulphonate or sulphamate functional groups. Thus any combination can be envisaged.

Without wishing to be tied to any given theory, the modification and/or occupation of these strategic positions by radicals may prevent their breakdown by the bacterial enzymes responsible for resistance implicated in the modifications to the structure of aminoglycosides. This could explain the remarkable antibacterial activity observed for these compounds.

According to a preferred embodiment of the invention, the identical or different residues $R_2$, $R_3$, $R_4$ and $R_5$ represent:

H;

an alkyl, haloalkyl or heteroalkyl group containing between 1 and 30 carbon atoms in a linear or branched chain;

one or more alkenyl or alkynyl groups containing between 2 and 30 carbon atoms in a linear or branched chain;

one or more cycloalkyl, cycloalkenyl or cycloalkynyl groups, substituted (such as, for example, a streptamine or 2-deoxystreptamine nucleus) or not, containing between 3 and 30 carbon atoms in a linear or branched chain;

one or more aryl or heteroaryl groups containing between 3 and 10 carbon atoms per ring;

an alkaryl or aralkyl group containing between 1 and 30 carbon atoms, the terms aryl and alkyl having the definitions below;

one or more alkoxy, thioalkyl, sulphonylalkyl or aminoalkyl groups containing between 1 and 30 carbon atoms in a linear or branched chain;

one or more alkoxyalkyl, alkylthioalkyl, alkylsulphonylalkyl, alkylaminoalkyl, alkylketoalkyl, aryl or alkyl alkylester groups containing between 1 and 30 carbon atoms in a linear or branched chain;

one or more heterocyclic groups containing between 5 and 10 carbon atoms per ring;

a sugar, an oligosaccharide or pseudo-oligosaccharide such as neamine or one of its derivatives. It should be noted that possible natural derivatives, already described, falling into this category are to advantage excluded from the field of protection of compounds as such;

an alkylcarbonyl or arylcarbonyl (—C(O)R) group, R being defined as $R_2$, $R_3$, $R_4$ and $R_5$ an alkyloxycarbonyl or aryloxycarbonyl (—C(O)OR) group, R being defined as $R_2$, $R_3$, $R_4$ and $R_5$;

an alkylcarbamoyl or arylcarbamoyl group (—C(O)NHR or (—C(O)NRR'), R and R' being identical or different and being defined as $R_2$, $R_3$, $R_4$ and $R_5$;

a sulphonyl group (—$SO_2R$), R being defined as $R_2$, $R_3$, $R_4$ and $R_5$;

an aminosulphonyl group (—$SO_2NHR$ or —$SO_2NHRR'$), R and R' being identical or different and being defined as $R_2$, $R_3$, $R_4$ and $R_5$, all the said groups possibly being substituted by one or more nitro, cyano, hydroxy, carboxy, carbonyl or amino groups, by one or more halogens or by one or more nitril, cyanhydrin, or aldehyde functions.

"Amine" is understood to mean a group containing a nitrogen atom. It could be a primary amine $NH_2$, a secondary amine NHR' or a tertiary amine NR'R". R' and R", which may be identical or different are defined as $R_2$, $R_3$, $R_4$ and $R_5$.

According to the invention, the term "alkyl" describes a linear or branched hydrocarbon radical of 1 to 30 carbon atoms, such as, for example, methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl. The alkyl group defined above may include one or more halogen atoms (fluorine, chlorine, bromine or iodine). In this case, we speak of a "haloalkyl" group. The alkyl group can also include heteroatoms selected from P, O, N, S and Se. In this case, we speak of a "heteroalkyl" group.

"Alkenyl" is taken to mean a linear or branched hydrocarbon chain of 2 to 30 carbon atoms including one or more double bonds. Examples of alkenyl groups are alkenyl groups which have only one double bond such as —CH—CH=CH—$CH_2$, $H_2C$=CH— (vinyl) or $H_2C$=CH—$CH_2$— (allyl).

"Alkynyl" is taken to mean a linear or branched hydrocarbon chain of 2 to 30 carbon atoms including one or more triple bonds. Examples of alkynyl groups are alkynyl groups having only one triple bond such as —$CH_2$—C≡CH.

"Cycloalkyl" describes saturated hydrocarbons groups which can be mono- or polycyclic containing 3 to 10 carbon atoms. These are, for example, monocyclic cycloalkyl groups such as cyclopropyl, cyclobutyl, cyclopentyl, cyclohexyl, cycloheptyl, cyclooctyl, cyclononyl, cyclodecyl, cycloundecyl and cyclododecyl.

"Cycloalkenyl" is taken by the invention to mean a group derived from a cycloalkyl group as defined above, having one or more double bonds, for example two double bonds. For example, it refers to the cyclohexene (one double bond) or cyclopenta-1,3-diene (two double bonds) group.

"Cycloalkynyl" is taken by the invention to mean a group derived from a cycloalkyl group as defined above, having one or more triple bonds, e.g. one triple bond.

The term "aryl" refers to an aromatic polycyclic or monocyclic hydrocarbon group containing 3 to 10 carbon atoms per ring, such as phenyl or naphthyl.

"Heteroaryl" refers to a polycyclic or monocyclic aromatic group containing between 3 and 10 carbon atoms per ring and including 1, 2 or 3 endocyclic heteroatoms per ring selected from P, O, N, S and Se. Examples are the furyl, thienyl, pyrrolyl, oxazolyl, isoxazolyl, thiazolyl, isothiazolyl, imidazolyl, pyrazolyl, oxadiazolyl, triazolyl, thiadiazolyl, pyridyl, pyridazinyl, pyrazinyl and triazinyl groups.

"Alkaryl" is taken to mean an alkyl group, substituted by an aryl group, these two groups being defined above.

"Aralkyl" is taken to mean an aryl group, substituted by an alkyl group, these two groups being defined above.

"Alkoxy" is taken to mean an O-alkyl group containing between 1 and 30 carbon atoms, particularly methoxy, ethoxy, propoxy and butoxy. "Alkoxyalkyl" is taken to mean an alkyl-O-alkyl group containing between 1 and 30 carbon atoms. The "thioalkyl" or "alkylthioalkyl", "sulphonylalkyl" or "alkylsulphonylalkyl" and "aminoalkyl" or "alkylaminoalkyl" groups contain in addition respectively one or more atoms of sulphur, one or more sulphonyl groups and one or more amine functions.

The term "heterocyclic group" refers to polycyclic or monocyclic, unsaturated or saturated carbon rings with 1, 2 or 3 endocyclic heteroatoms chosen from P, O, N, S and Se. These are generally derivatives of the heteroaryl groups described above. Examples of unsaturated heterocyclics are dihydrofuryl, dihydrothienyl, dihydropyrrolyl, pyrrolinyl, oxazolinyl, thiazolinyl, imidazolinyl, pyrazolinyl, isoxazolinyl, isothiazolinyl, oxadiazolinyl, pyranyl and the mono-unsaturated derivatives of piperidine, dioxane, piperazine, trithiane, morpholine, dithiane, thiomorpholine, and tetrahydropyridazinyl, tetrahydropyrimidinyl, and tetrahydrotriazinyl.

Because of processes used to advantage in this invention, $R_4$ (in position 6) and $R_3$ (in position 3'), possibly $R_2$ (in position 4'), and possibly $R_5$ (in position 5), are preferably identical.

According to a preferred embodiment, $R_2$ and/or $R_3$ and/or $R_4$ and/or $R_5$ are selected from the following group: naphthyl-2-methylene (2NM), naphthyl-1-methylene (1NM), and hexyl.

The disubstituted or trisubstituted compounds particularly preferred according to the invention are as follows:

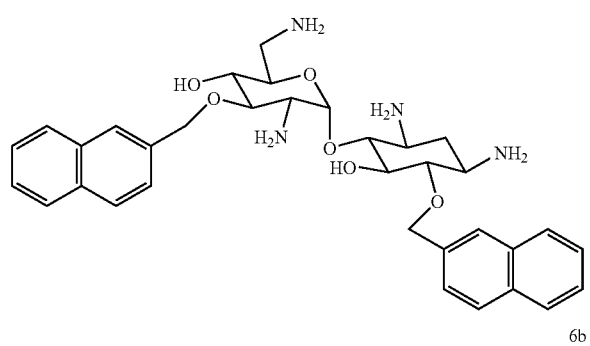

6a

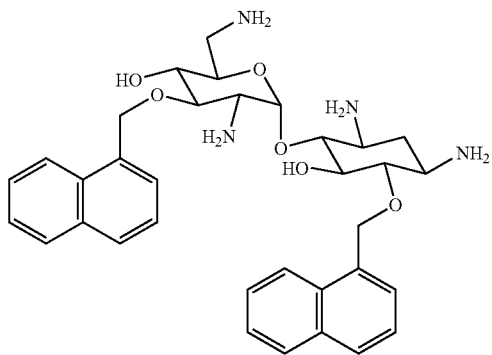

6b

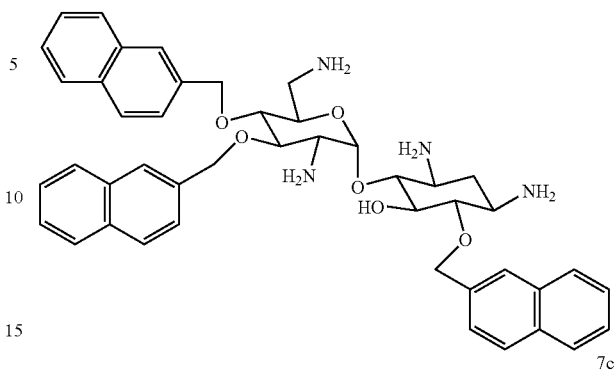

7a

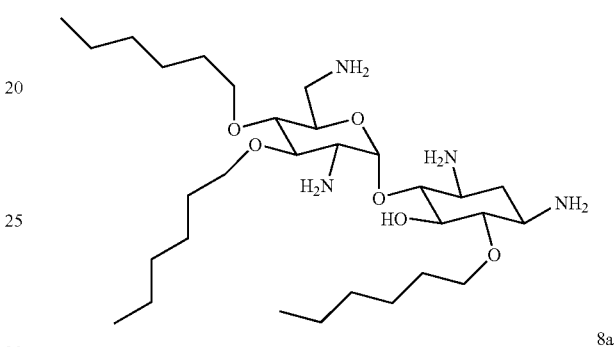

7c

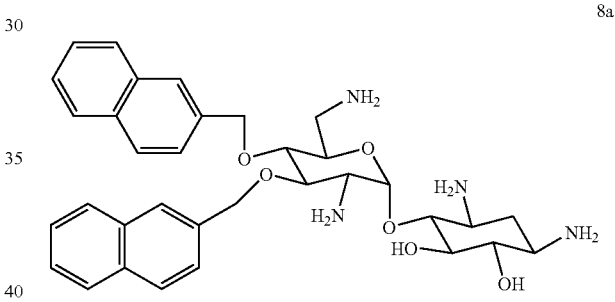

8a

Compound 6a is 3',6-O,O'-di(naphthyl-2-methylene) neamine.
Compound 7a is 3',4',6-O,O',O''-tri(naphthyl-2-methylene) neamine.
Compound 6b is 3',6-O,O'-di(naphthyl-1-methylene) neamine.
Compound 7c is 3',4',6-O,O',O''-tri-n-hexyl neamine.
Compound 8a is 3',4'-O,O'-di-(naphthyl-2-methylene) neamine.

More generally and relative to the 2NM derivative, compounds with the following formulae were easily prepared and had the desired biological activity explained below:

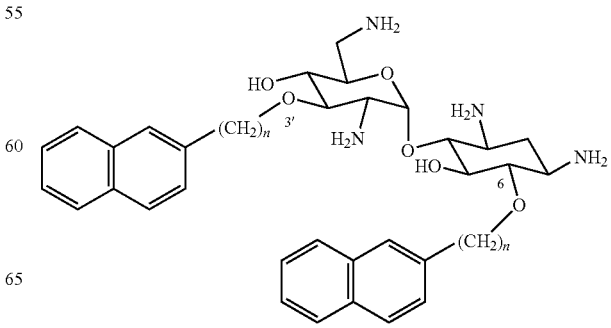

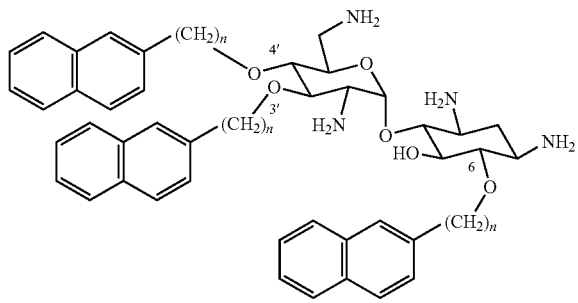

n = 3, 4, 6

The following compounds in particular can be mentioned:
3',6-O,O'-di(naphthyl-2-propyl) neamine;
3',4',6-O,O',O"-tri(naphthyl-2-propyl) neamine;
3',6-O,O'-di(naphthyl-2-butyl) neamine;
3',4',6-O,O',O"-tri(naphthyl-2-butyl) neamine.

Apart from all these compounds being new, it has been shown in the context of this invention that they could be of interest for a therapeutic application. For this reason and according to another aspect, this invention concerns the use of a compound as described above as a medicinal product and a pharmaceutical composition containing it.

To advantage, in such a composition, the compound according to the invention is in the form of a pharmaceutically acceptable salt, particularly a hydrochloride or methylsulphonate.

Of course, such a composition can also contain any excipient or pharmaceutically inert vehicle, and possibly one or more other active ingredients. For cocktails of antibiotics, a preferred active substance is an antibiotic of another class, preferably a β-lactam or a fluoroquinolone.

As already stated, the compounds according to the invention can be used to advantage in the preparation of medicinal products intended for prophylaxis or the treatment of bacterial infections. These bacterial infections can be due to wild-type or resistant Gram positive bacteria, such as *Staphylococcus aureus*, or Gram negative bacteria, such as *Escherichia coli, Pseudomonas aeriginosa, Acinetobacter lwoffi, Klebsiella pneumoniae, Enterobacter aerogenes, Citrobacter amalonaticus*. The compounds according to the invention can be remarkably active both against sensitive strains and strains considered as resistant particularly to the classic aminoglycosides such as neamine or neomycin.

According to another aspect, this invention also concerns the synthetic process to obtain the derivatives from neamine or paromamine, di- or tri-substituted at the desired positions.

Thus, the invention has brought to light different synthetic pathways. These different pathways have the following points in common:

the starting substance, which is paromamine ($R_1$=OH in the 6' position) or neamine ($R_1$=$NH_2$ in the 6' position);

a first stage consisting of protecting the alcohol and/or amine functional groups in positions 1, 3, 2', 6', to advantage by tritylation;

then modification of the hydroxyl group in the 6 and/or 3' position;

and a final stage deprotecting positions 1, 3, 2' and 6'.

The first stage is well known as it consists of protecting the functional groups, particularly amines, in the 1, 3, 2' and 6' positions. According to a process described in document WO 2005/060573, this stage can be carried out using trityl groups (triphenylmethyl), 4-monomethoxytrityl, 4',4'-dimethoxytrityl or 4,4',4"-trimethoxytrityl), in the presence of a base having a $pK_a$ greater than that of the amine functions present in these positions, if the latter are protonated in the starting derivative, paromamine or neamine.

The final stage of such a procedure to obtain the required derivatives is also itself known as it consists of deprotecting the amine and hydroxyl functional groups by treating in an acid medium, for example with a TFA/anisole mixture.

The objective of intermediate stages is to introduce the radicals into the required positions, particularly by alkylation. Temporary protection stages may be necessary depending on the reactivity of the groups at the different positions.

According to a first synthetic pathway (pathway A), the protected product reacts with a halogenated derivative RX (for example X=Cl, Br or I) or a sulphonylated derivative (for example X=mesyl or tosyl) bearing the R group to be introduced in position 6, possibly in position 3', and possibly in position 4'. R has the same definition as that given for $R_2$, $R_3$ and $R_4$ for this invention.

This reaction occurs in the presence of a base capable of deprotonating the targeted hydroxyl groups, for example sodium hydride. The temperature, the solvent, the nature of the halogenated or sulphonylated derivative and the proportions of the reagents are chosen depending on the required selectivity (alkylation in position 6 and/or 3' and/or 4'). N,N-dimethylformamide (DMF) is the solvent generally used but the use of, for example, a DMF-tetrahydrofuran (THF) mixture slows the reaction and can improve the selectivity required. In certain cases, tetrabutylammonium iodide can be added to the reaction medium to accelerate the reaction.

In this case, derivatives monosubstituted at 6, disubstituted at 3'+6 and trisubstituted at 3'+4'+6 are obtained simultaneously. In addition, according to the simplest reaction plan, these derivatives have identical $R_3$ (3' position), $R_4$ (6 position) and $R_2$ (4' position) residues.

The corresponding reaction scheme is shown below for tetratritylated neamine 9:

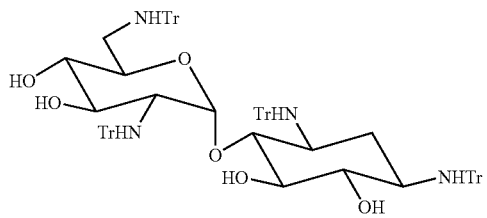

11
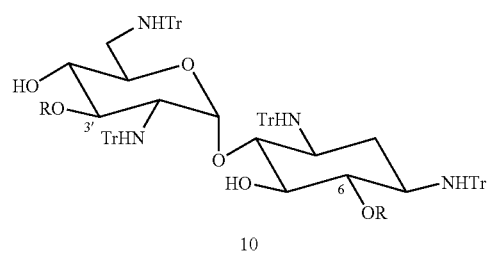
10
12
-continued
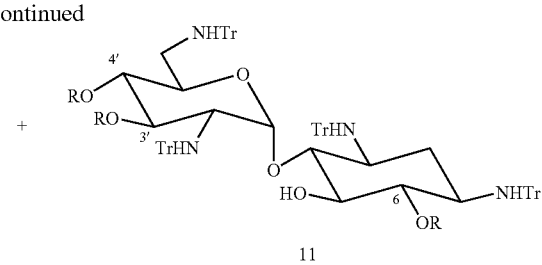
11
| TFA, anisole
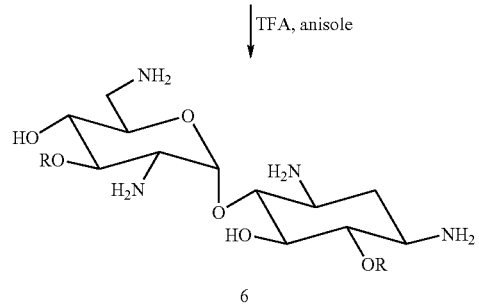
6
| TFA, anisole
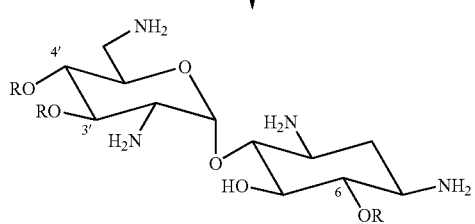
7
It has been observed that quite unexpectedly, the final detritylation stage in an acid medium of the derivative 11a used to prepare the derivative 7a also produces the derivative 8a, alkylated in the 3'+4' positions, when the reaction time is increased (24 hours). The corresponding reaction scheme is shown below:
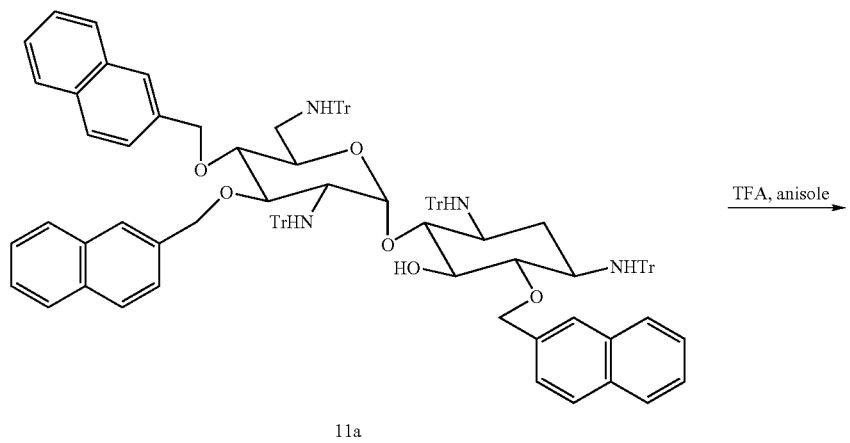
11a
TFA, anisole
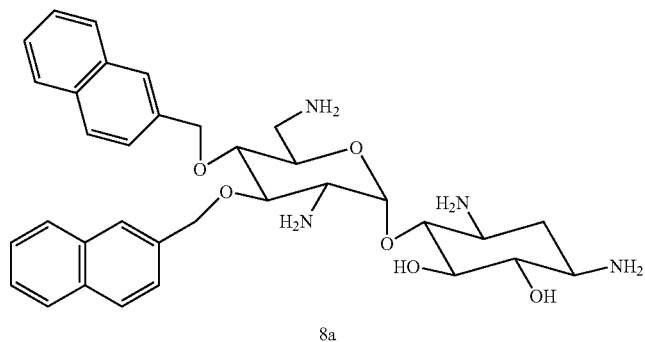
8a In the context of the invention, these derivatives have proved to be active antibacterial agents.

The derivative monosubstituted at 6 is very interesting because it serves as intermediate product in two other synthetic pathways (pathways B and C).

According to a second embodiment (pathway B), the derivative monosubstituted at 6 bearing the R group is reacted with a derivative R'X which may be halogenated (e.g. X=Cl, Br, I) or sulphonylated (e.g. X=mesyl or tosyl), bearing the R' group to be introduced in the 3' position, and possibly in the 4' position. The use of a distinct compound R"X can be envisaged for the 4' position. Again R' and R" have the same definition as that given for $R_2$, $R_3$ and $R_4$ for this invention.

At the end of this reaction, derivatives are obtained simultaneously disubstituted in the 3'+6 positions and trisubstituted in the 3'+4'+6 positions, with $R_3$ (position 3') and $R_4$ (position 6) residues which may be different, and $R_3$ (position 3') and $R_2$ (position 4') residues which are identical or possibly different.

These reactions occur in the presence of a base capable of deprotonating the targeted hydroxyl groups, e.g. sodium hydride. The temperature, the solvent, the nature of the halogenated or sulphonylated derivative and the proportions of the reagents are chosen depending on the required selectivity (alkylation in position 6 and/or 3' and/or 4'). N,N-dimethylformamide (DMF) is the solvent generally used but the use of, for example, a DMF-tetrahydrofuran (THF) mixture slows the reaction and can improve the required selectivity. In certain cases, tetrabutylammonium iodide can be added to the reaction medium to accelerate the reaction.

The corresponding reaction scheme is shown below concerning tetratritylated neamine:

According to an alternative embodiment (pathway C), the derivative monosubstituted at 6 bearing the R group is first protected at the 3' position by using a protector group (Z) and is then reacted with a derivative R'X which may be halogenated (e.g. X=Cl, Br, or I) or sulphonylated (e.g. X=mesyl or tosyl), bearing an R' group to be introduced in the 4' position. R' has the same definition as that given for $R_2$, $R_3$ and $R_4$ for this invention.

Protection in the 3' position can be provided using an acid-labile group Z by reaction with a derivative which may be halogenated (e.g. X=Cl, Br or I) or sulphonylated (e.g. X=mesyl or tosyl), particularly of the arylmethylene (ArCH$_2$X, Ar=2-naphthyl, 1-naphthyl, anthracenyl, fluorenyl, pyrenyl, etc.) or silylated (Z=tert-butyldimethylsilyl, triethylsilyl, etc.) type.

The reaction occurs in the presence of a base capable of deprotonating the targeted hydroxyl groups, e.g. sodium hydride. The temperature, the solvent, the nature of the halogenated or sulphonylated derivative and the proportions of the reagents are chosen depending on the selectivity required (protection by alkylation in the 3' position to introduce an acid-labile protector group then alkylation in the 4' position). N,N-dimethylformamide (DMF) is the solvent generally used but the use of, for example, a DMF-tetrahydrofuran (THF) mixture slows the reaction and can improve the selectivity required. In certain cases, tetrabutylammonium iodide can be added to the reaction medium to accelerate the reaction.

At the end of this reaction, derivatives are obtained disubstituted at 4'+6, with the residues $R_2$ (4' position) and $R_4$ (6 position) possibly different.

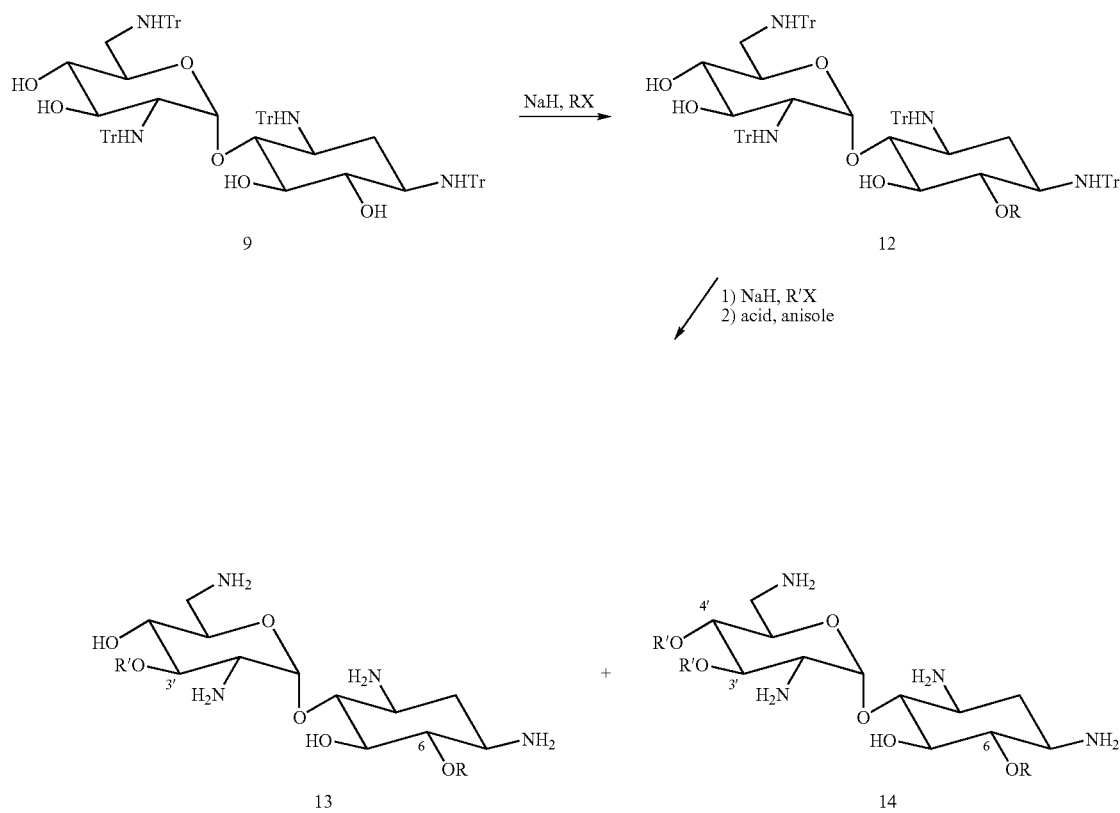

The corresponding reaction scheme is shown below for tetratritylated neamine:

hydride. The temperature, the solvent, the nature of the halogenated or sulphonylated derivative and the proportions of the reagents are chosen depending on the selectivity required (identical or different alkylation in the 3' and 4' positions with a first alkylation in the 3' position). N,N-dimethylformamide (DMF) is the solvent generally used but the use of, for example, a DMF-tetrahydrofuran (THF) mixture slows the reaction and can improve the selectivity required. In certain cases, tetrabutylammonium iodide can be added to the reaction medium to accelerate the reaction.

At the end of this second stage and according to the simplest reaction scheme, derivatives are obtained disubstituted at 3'+4', with residues $R_3$ (3' position) and $R_2$ (4' position) being identical. However, these residues may be different if alkylation is performed in two steps: a first alkylation in the 3' position with a given residue R, then a second alkylation step in the 4' position with a residue R' differing from R.

The corresponding reaction scheme is shown below for tetratritylated neamine:

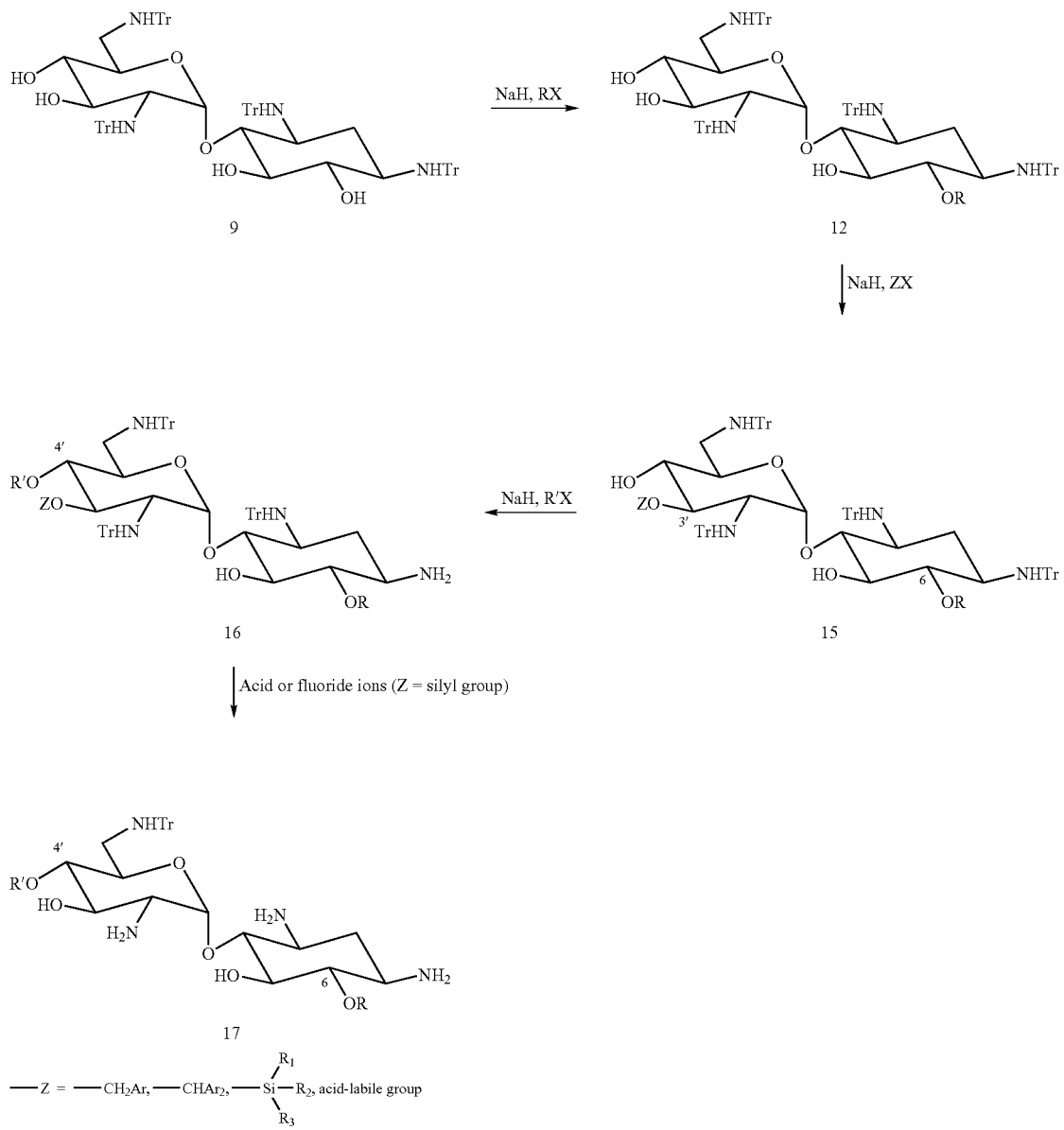

Lastly, according to a final embodiment, the modification at the 6 position consists of introducing a protector group (Z). This protection can be provided using an acid-labile group Z by reaction with a derivative which may be halogenated (e.g. X=Cl, Br or I) or sulphonylated (e.g. X=mesyl or tosyl), particularly of the arylmethylene (ArCH$_2$X, Ar=2-naphthyl, 1-naphthyl, anthracenyl, fluorenyl, pyrenyl, etc.) or silylated (Z=tert-butyldimethylsilyl, triethylsilyl, etc.) type.

The protected derivative is then reacted with a derivative RX which may be halogenated (e.g. X=Cl, Br or I) or sulphonylated (e.g. X=mesyl or tosyl), bearing the R group to be introduced in the 3' position and the 4' position. R has the same definition as that given for $R_2$, $R_3$ and $R_4$ for this invention.

These reactions occur in the presence of a base capable of deprotonating the hydroxyl groups targeted, e.g. sodium

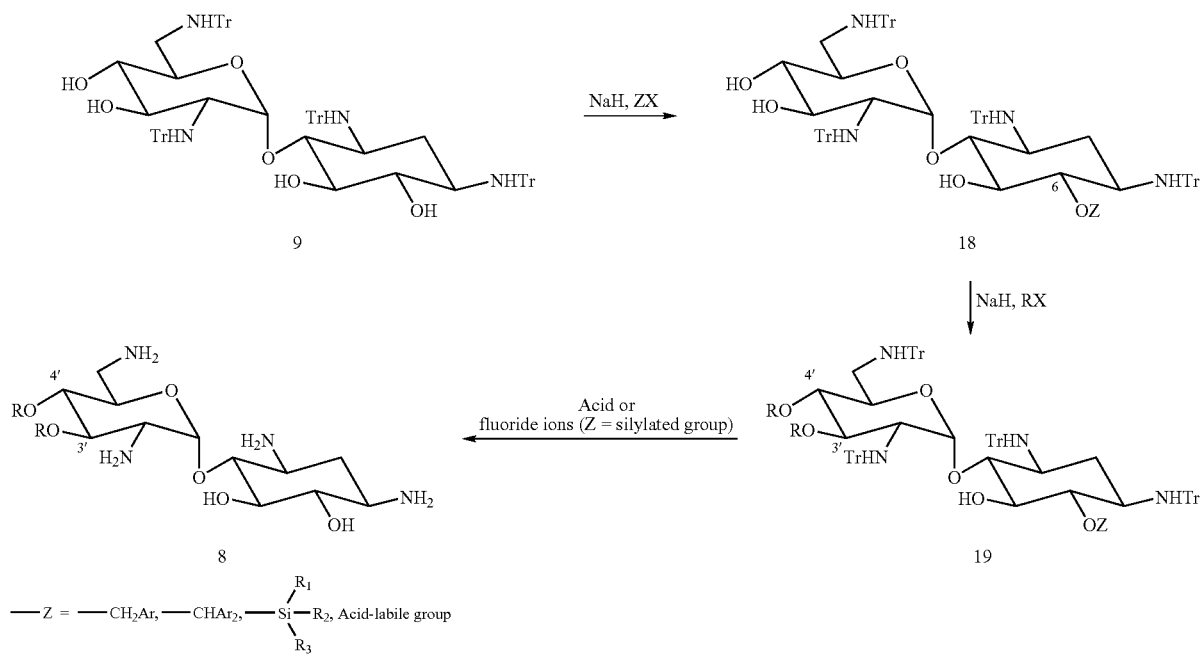

Another pathway synthesising compounds of interest according to the invention consists of using a biphasic process in the presence of a phase transfer catalyst. Compared with the processes in solution described below, this type of process is highly selective, producing a large majority of the product the nature of which depends on the experimental conditions applied.

Thus, depending on the nature of the phase transfer catalyst present, two main synthetic pathways have been followed, one based on modification of the hydroxyl functional group in the 3' position and the other on modification of the hydroxyl group in the 6 position.

According to a first aspect, alkylation occurs selectively in the 3' position (right hand pathway in the diagram below), or in the 3'+6 positions (left hand pathway in the diagram below), depending on the quantity of alkyl halide (RX) present.

The alkylation occurs by phase transfer with an aqueous phase containing sodium hydroxide (30 to 50%) and an organic phase composed of toluene (or for example dichloromethane) and containing the dissolved derivative 9. The phase transfer catalyst, here tetrabutylammonium iodide or bromide, is then added followed by the alkyl halide (RX), e.g. paramethoxybenzyl chloride (PMBCl).

Under a first condition which consists of limiting the quantity of alkyl halide (e.g. PMBCl) and the quantity of phase transfer catalyst, it is possible to promote the formation of the derivative with the functional group in the 3' position. The reaction can be performed at room temperature or at a higher temperature. After isolating the 3' derivative formed, it can be bisalkylated under different conditions in the 4' and 6 positions then deprotected in the presence of TFA and anisole to lead to the derivative bisalkylated in the 4' and 6 positions. Alternatively it can be trisalkylated under different conditions in the 4', 5 and 6 positions then deprotected in the presence of TFA and anisole to lead to the derivative trisalkylated in the 4', 5 and 6 positions.

Under another condition which consists of only performing the first alkylation stage by phase transfer and using a greater quantity of alkyl halide (e.g. PMBCl, 1NMBr, 2NMBr), it is possible to promote formation of the derivative bisalkylated in the 3',6 positions.

If the group previously introduced into the 3' position is stable in the TFA/anisole mixture, mixed 3',4',6 trialkylated derivatives (R≠R') can also be prepared after deprotection.

These different pathways are shown in the diagram below:

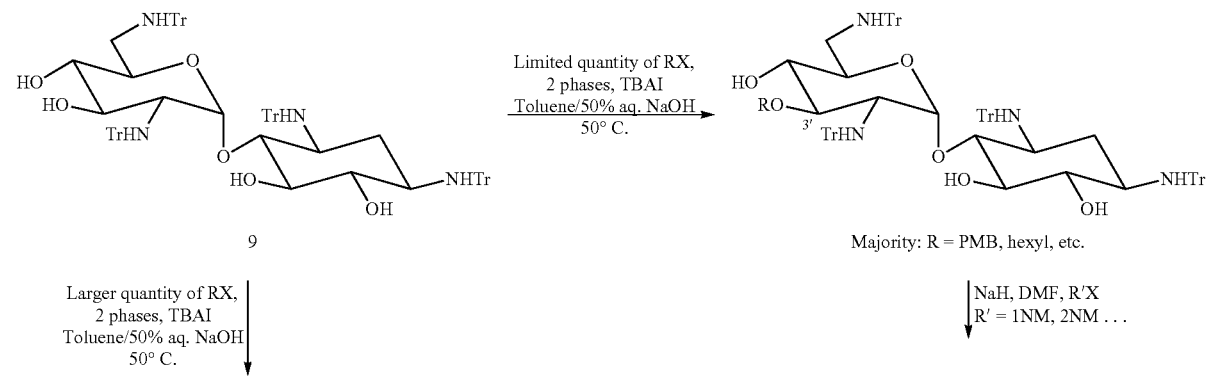

-continued
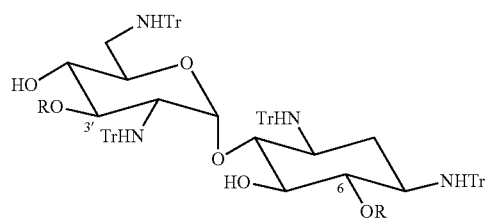
Very large majority
R = PMB, 1NM, 2NM
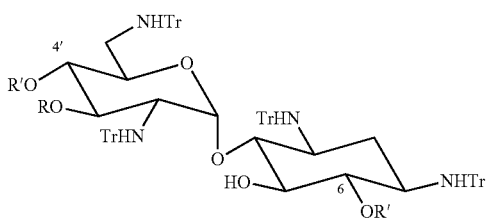
R = hexyl
R' = 1NM, 2NM ...
TFA, anisole
R = PMB
R' = 1NM, 2NM ...
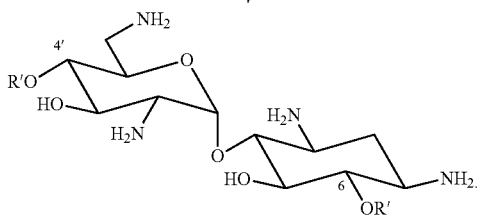
This diagram can, for example, serve for the synthesis of:
the 4',6-di-2NM derivative of neamine=

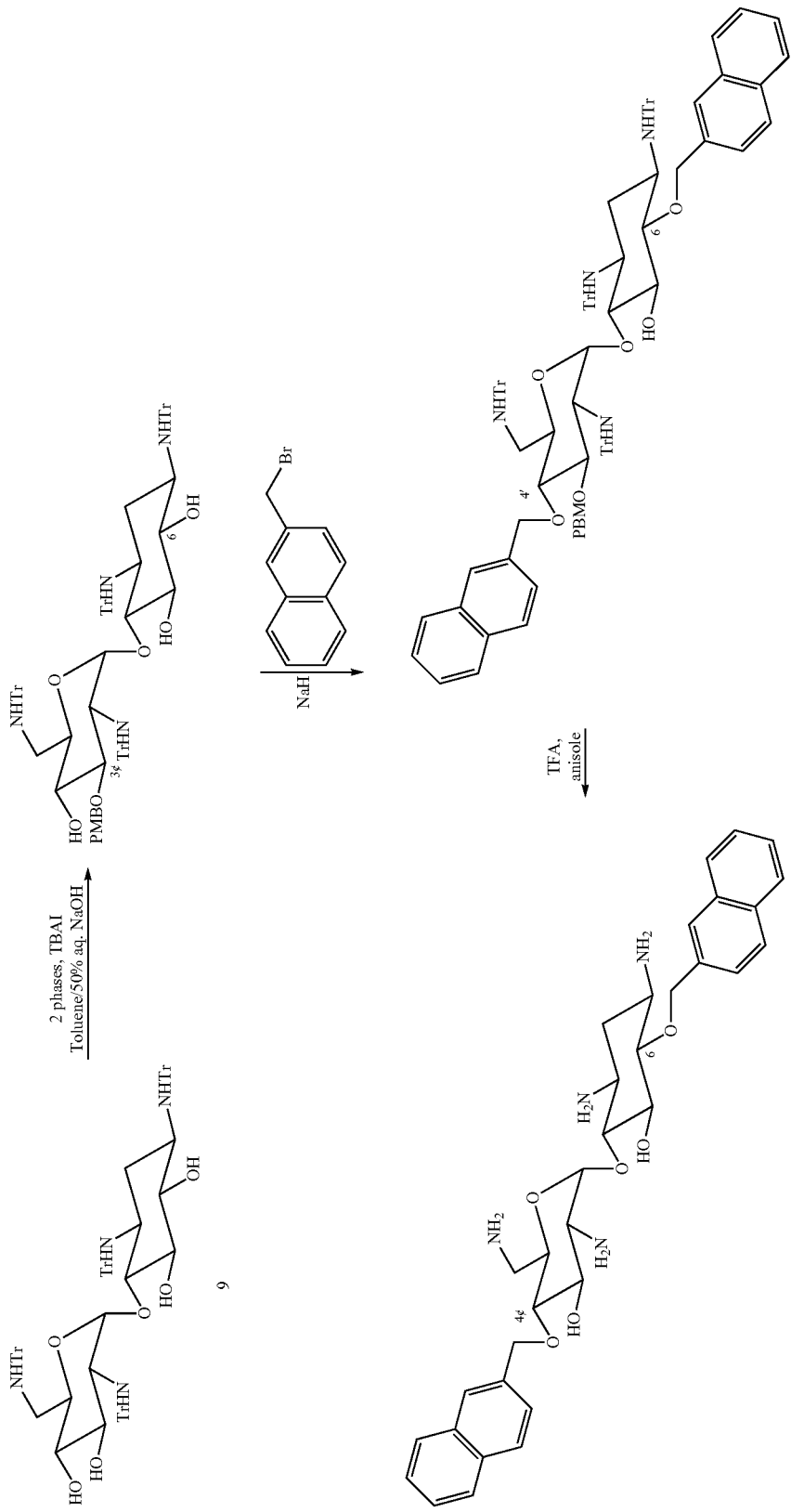

the 3',6-di-2NM derivative in the paromamine series=

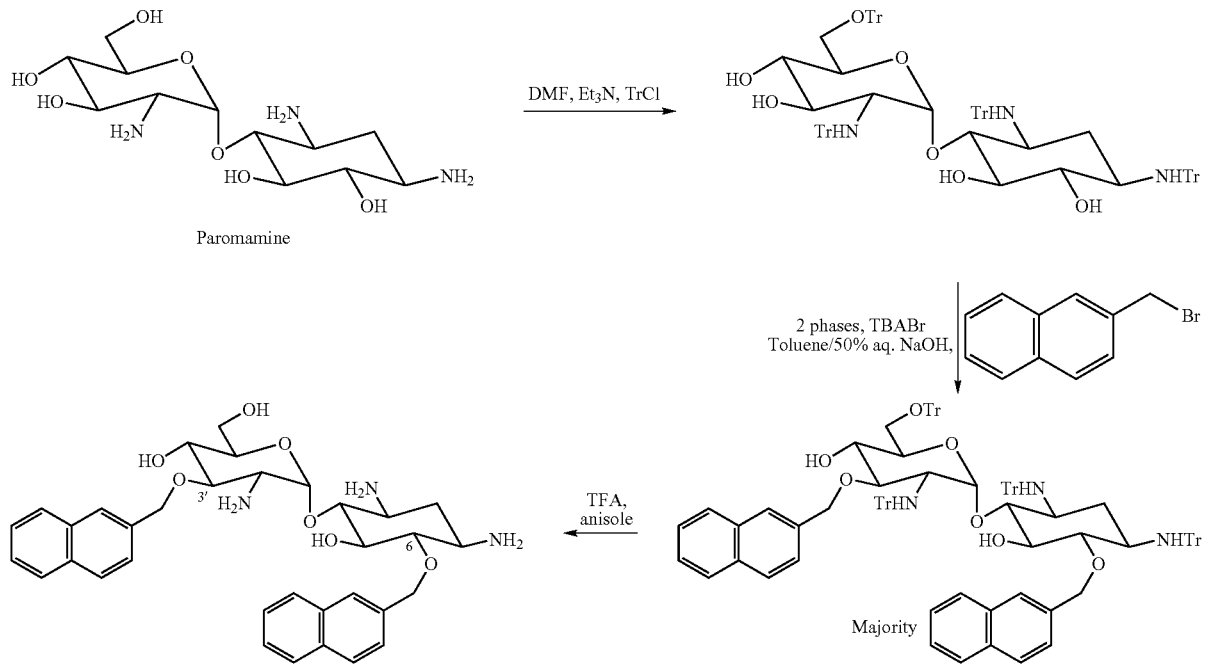

the 3',6-di-1NM derivative in the neamine series=

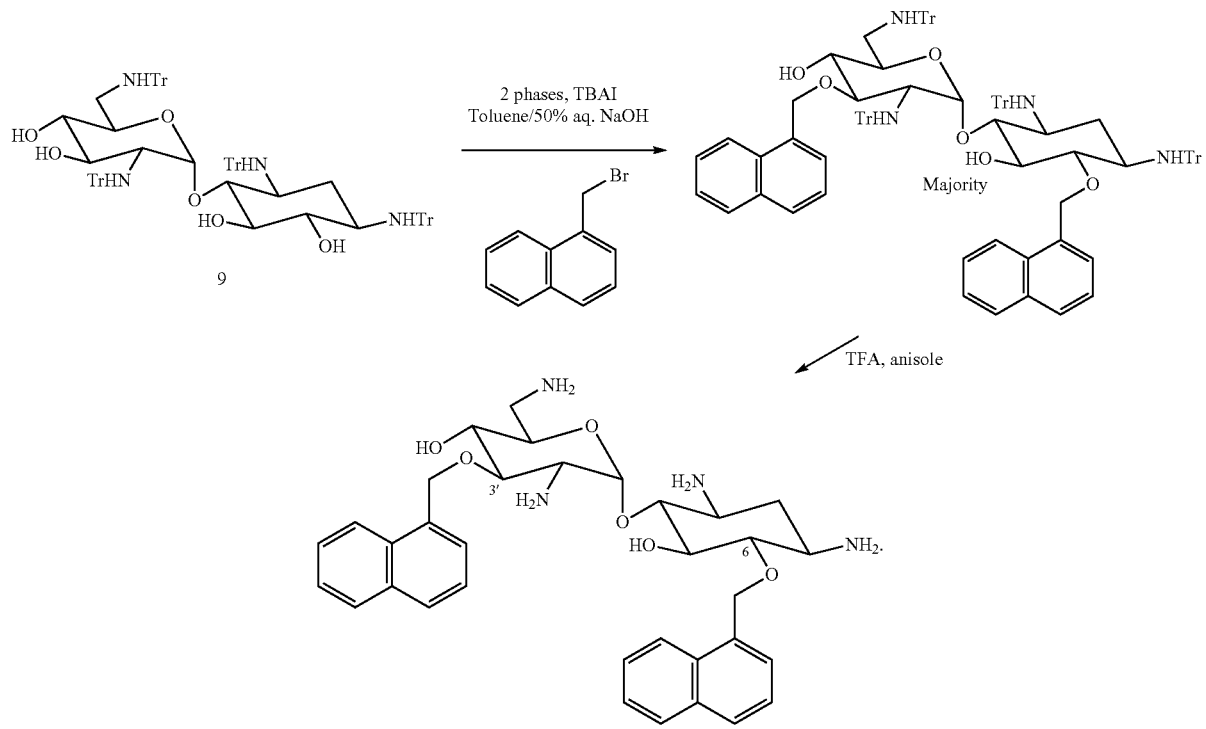

According to a second aspect, the alkylation occurs selectively in the 6 position (right hand pathway in the diagram below), or in the 3'+4'+6 positions (left hand pathway in the diagram below), depending on the quantity of alkyl halide (RX) present:

The alkylation occurs by phase transfer with an aqueous phase containing sodium hydroxide (30 to 50%) and an organic phase composed of toluene (or for example dichloromethane) and containing the dissolved derivative 9. The phase transfer catalyst, here tetrabutylammonium (or tetramethyl- or triethyl-ammonium, etc.) fluoride (or chloride or hydrogen phosphate etc) is then added followed by the alkyl halide, e.g. para-methoxybenzyl chloride (PMBCl).

Under a first condition which consists of limiting the quantity of alkyl halide (e.g. PMBCl) and the quantity of phase transfer catalyst, it is possible to promote the formation of the derivative with the functional group in the 6 position. After isolating the 6 derivative formed, it can be bisalkylated under different conditions in the 3' and 4' positions then deprotected in the presence of TFA and anisole to lead to the derivative bisalkylated in the 3' and 4' positions. Alternatively it can be trisalkylated under different conditions in the 3', 4' and 5 positions then deprotected in the presence of TFA and anisole to lead to the derivative trisalkylated in the 3', 4' and 5 positions.

If the group previously introduced into the 6 position is stable in the TFA/anisole mixture, mixed 3',4',6 trialkylated derivatives (R≠R') can also be prepared after deprotection.

Under another condition which consists of only performing the first alkylation stage by phase transfer and using a greater quantity of alkyl halide (e.g. PMBCl, 1NMBr, 2NMBr), it is possible to promote the formation of the derivative trisalkylated in the 3'+4'+6 positions.

These different pathways are shown in the diagram below:

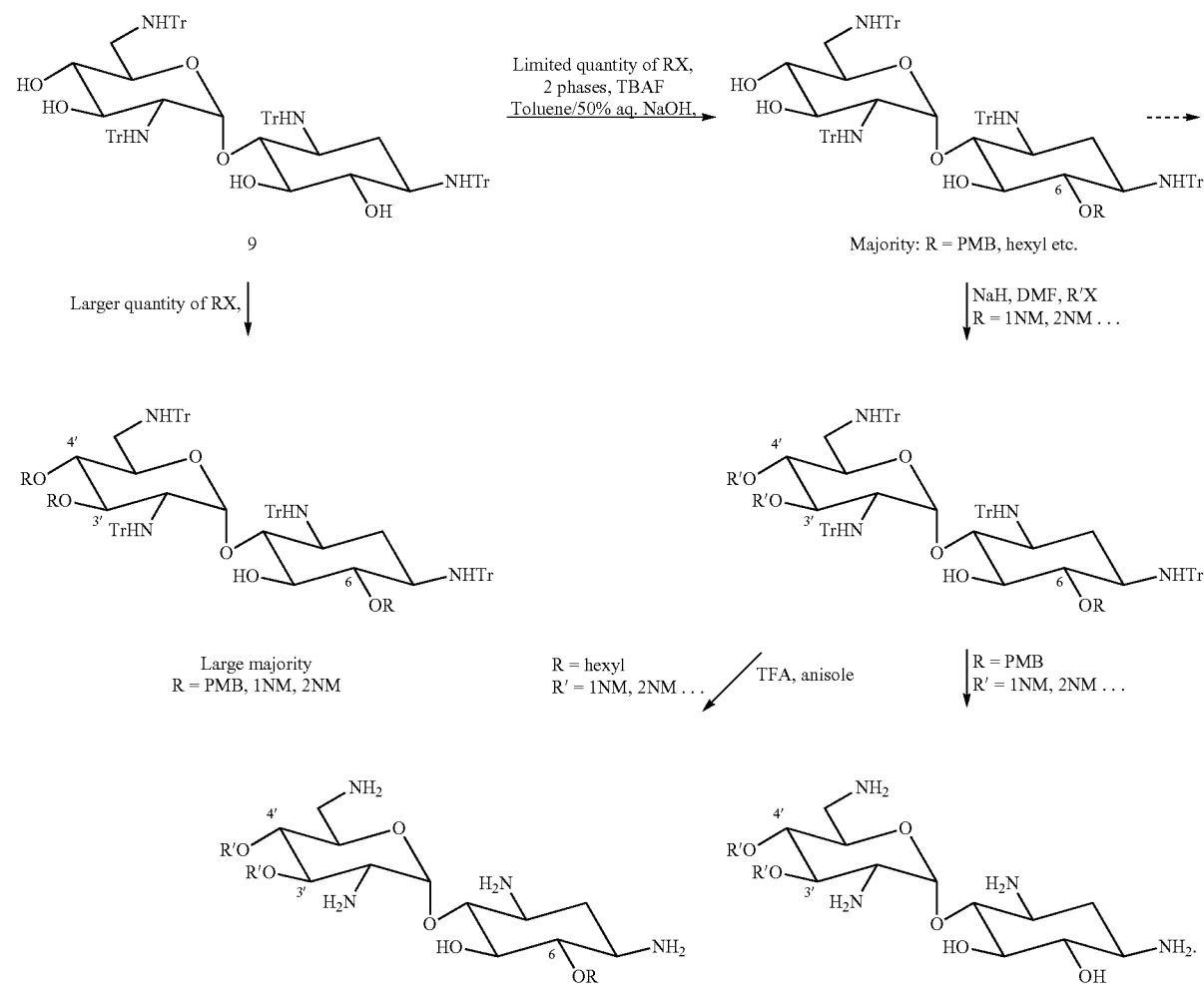

This diagram can, for example, serve for the synthesis of: the N-tetratritylated 6-mono-2NM derivative of neamine=

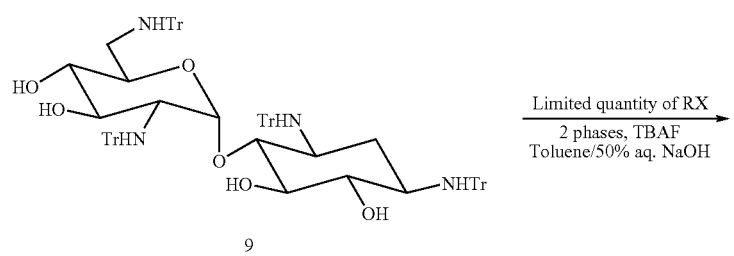

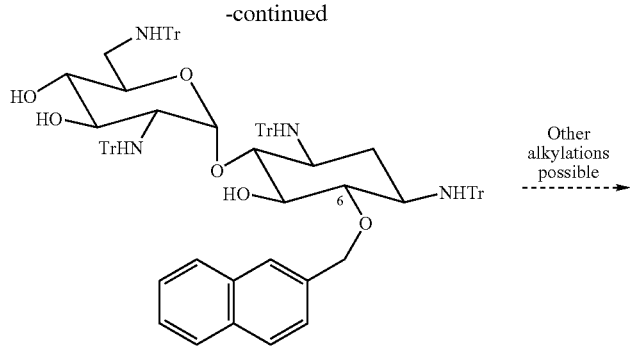

the 3',4',5-tri-2NM derivative=

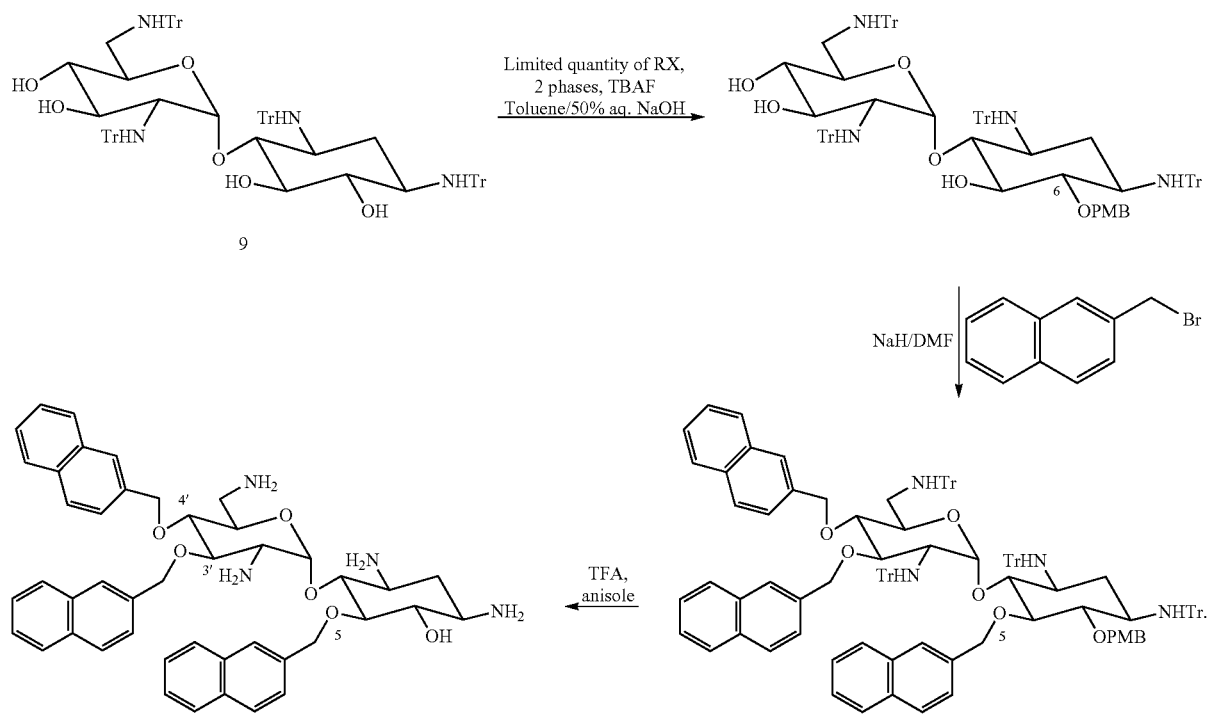

These different reaction schemes were described earlier in relation to the alkylation reactions. Nevertheless the principle remains the same for the preparation of aryl derivatives, ester, carbonate, carbamate, sulphonate or sulphamate derivatives.

For these derivatives, the alkylation and/or protection reactions described above are replaced by arylation, acylation, carbonatation, carbamoylation, sulphonylation, aminosulphonylation and/or silylation reactions well known to those skilled in the art. As an example, acylation reactions are performed in dichloromethane with an acid anhydride or chloride, in the presence of a base such as pyridine, N,N-dimthylaminopyridine, or triethylamine. It is also possible to envisage carrying out the acylation enzymatically.

Moreover, it seems that the R or R', even R" groups mentioned in these reaction schemes can correspond to the $R_2$, $R_3$, $R_4$ and $R_5$ groups present in the final compound. Nevertheless, the nature of these groups can be modified by two mechanisms:

Alkylation reactions (and also arylation, acylation, carbonatation, carbamoylation, sulphonylation or aminosulphonylation) may be arranged and the nature of R modified between each stage (between the introductions to the different positions).

The group put into position 3' or 4' or 6 or 5 can be introduced in several stages. After introducing R or R' to the required position, this residue can thus be modified by successive reactions.

EXAMPLES OF EMBODIMENTS

The invention and the advantages resulting from it are better illustrated by the following examples. However, these examples are in no case limiting.

This invention will be further illustrated with the help of compounds dialkylated in the 3' and 6 positions or trialkylated in the 3', 4' and 6 positions, obtained at the end of synthesis according to pathway A as described above and summarised here:

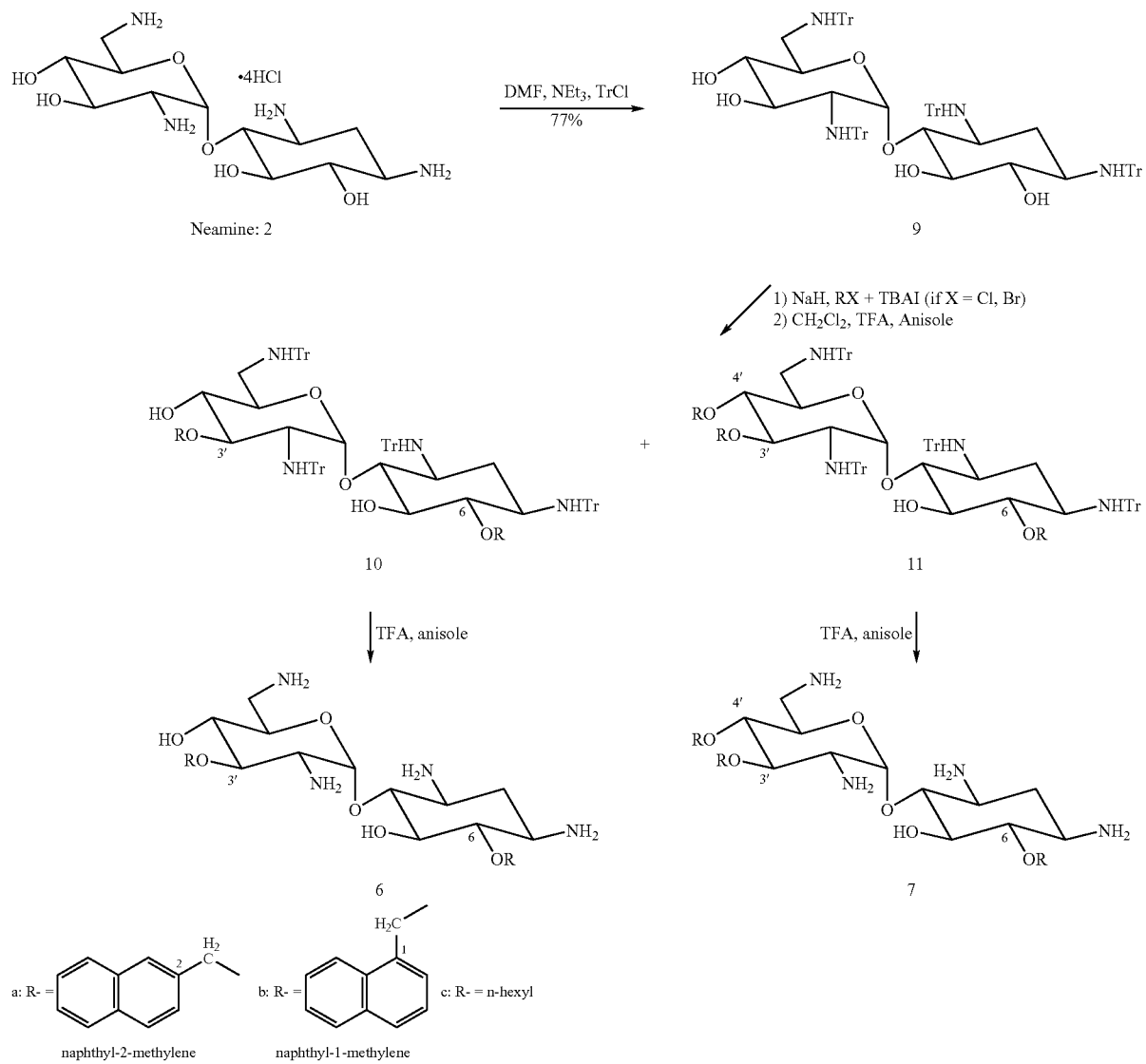

Experimental Part

I—Synthesis of the Derivatives

A/ Classic Pathway:

1/ Synthesis of the 3',6-di(naphthyl-2-methylene) neamine 6a and 3',4',6-tri(naphthyl-2-methylene) neamine 7a derivatives The tritylated derivative of neamine 9 (2.0 g, 1.55 mmol) was dissolved in anhydrous DMF (20 mL), under argon. Sodium hydride (60%, 217 mg, 5.42 mmol), tetrabutylammonium iodide (572 mg, 1.55 mmol) and 2-(bromomethyl)naphthalene (857 mg, 3.87 mmol) were added successively. The mixture was continually stirred for 24 h at room temperature, then 150 mL of dichloromethane were added. The organic phase was then washed with 200 mL of water then dried on magnesium sulphate. After evaporation of the solvents under reduced pressure, the residue obtained was subjected to chromatography on alumina gel using a 50/50 cyclohexane/dichloromethane mixture. The product 10a (980 mg, 0.62 mmol, 40%) and the product 11a (1.01 g, 0.59 mmol, 38%) were obtained after separation and evaporation of the solvents under reduced pressure. Compound 10a: MS (FAB$^+$, NBA) m/z=1594 [M+Na]$^+$, compound 11a: MS (FAB$^+$, NBA) m/z=1735 [M+Na]$^+$ The compound 10a (602 mg, 0.39 mmol) and the compound 11a (121 mg, 0.07 mmol) were respectively dissolved in a mixture of dichloromethane and trifluoroacetic acid (v/v: 1/1) to which a small quantity of anisole was added. After 12 hours reacting at room temperature, the solvents were evaporated under reduced pressure and water/diethylether extraction was performed. After concentration of the aqueous phase under reduced pressure, the residue was subjected to C18 reversed-phase column chromatography with a water/methanol elution gradient of between 100/0 and 50/50. The compounds thus obtained were passed through an ion exchange column with water as eluent then with a water/ammonia mixture (98/2). After evaporation of the solvent under reduced pressure, the compounds were dissolved in a 1N aqueous solution of HCl. The compound 6a and the compound 7a were obtained in the form of hydrochlorides after concentration and drying.

Compound 6a: Yield=70%; NMR $^1$H (400 MHz, D$_2$O) δ ppm=7.84-7.89 (m, 8H, H-naphthyl), 7.47-7.50 (m, 6H, H-naphthyl), 5.86 (d, J=3.6 Hz, 1H, H-1'), 5.05 (d, J=12.0 Hz, 1H, CH$_2$-naphthyl), 5.02 (d, J=12.0 Hz, 1H, CH$_2$-naphthyl), 4.88 (d, J=12.0 Hz, 1H, CH$_2$-naphthyl), 4.85 (d, J=12.0 Hz, 1H, CH$_2$-naphthyl), 4.04 (dd, J=8.5 et 10.4 Hz, 1H, H-3'), 3.96 (m, 1H, H-5'), 3.91 (dd, J=10.0 Hz, 1H, H-4), 3.82 (dd, J=9.2 Hz, 1H, H-5), 3.65 (dd, J=9.2 Hz, 1H, H-4'), 3.58 (dd, J=9.2 Hz, 1H, H-6), 3.45 (dd, J=3.6 and 10.4 Hz, 1H, H-2'), 3.43-3.28 (m, 3H, H-3, H-6'b, H-1), 3.22 (dd, J=9.6 and 12.8 Hz, 1H, H-6'a), 2.42 (ddd, J=4.0 and 12.4 Hz, 1H, H-2 eq.), 2.01 (ddd, J=12.4 Hz, 1H, H-2 ax.); NMR $^{13}$C (100 MHz, D$_2$O) δ ppm=132.9-134.6 (C-naphthyl), 126.3-128.6 (CH-naphthyl), 95.8 (C-1'), 79.8 (C-6), 77.5 (C-4), 75.6 (C-5 and C-3'), 75.1 (CH$_2$-naphthyl), 70.9 (C-4'), 69.9 (C-5'), 52.6 (C-2'), 48.8 (C-1), 48.3 (C-3), 39.8 (C-6'), 28.1 (C-2); MS (DCI$^+$) m/z=603 [M+H]$^+$, 463, 303, 141; HRSM (ESI$^+$): [M+H]$^+$ m/z theoretical=603.3183, found=603.3186, [M+Na]$^+$ m/z theoretical=625.3002, found=625.3006.

Compound 7a: Yield=65%, NMR $^1$H (400 MHz, MeOD) δ ppm=7.39-7.97 (m, 21H, H-naphthyl), 6.03 (d, J=3.6 Hz, 1H, H-1'), 4.94-5.29 (m, 6H, CH$_2$-naphthyl), 3.57-3.59 (m, 2H, H-3', H-5'), 4.20 (dd, J=9.6 Hz, 1H, H4), 4.08 (dd, J=9.2 Hz, 1H, H-5), 3.65-3.74 (m, 2H, H-6, H-4'), 3.49-3.56 (m, 2H, H-3, H-2'), 3.35-3.42 (m, 2H, H-6'b, H-1), 3.17 (dd, J=9.6 and 13.2 Hz, 1H, H-6'a), 2.46 (ddd, J=4.0 and 12.4 Hz, 1H, H-2 eq.), 2.01 (ddd, J=12.8 Hz, 1H, H-2 ax.); NMR $^{13}$C (100 MHz, MeOD) δ ppm=133.1-135.4 (C-naphthyl), 125.3-127.9 (CH-naphthyl), 95.2 (C-1'), 80.5 (C-6), 78.9 and 78.5 (C-4 and C-4'), 77.5 (C-3'), 76.3 (C-5), 74.7 and 74.4 (CH$_2$-naphthyl), 69.7 (C-5'), 53.4 (C-2'), 49.5 (C-1), 48.6 (C-3), 40.3 (C-6'), 29.5 (C-2); SM (DCI$^+$): m/z=743 [M+H]$^+$, 603 [M+H-(naphthylmethylene)]$^+$, 441, 303, 141; HRSM (ESI$^+$): [M+H]$^+$ m/z theoretical=743.3809, found=743.3810, [M+Na]$^+$ m/z theoretical=765.3628, found=765.3628.

2/Synthesis of the 3',4',6-tri-n-hexyl neamine derivative 7c

The compound 7c was synthesised according to the method described for compounds 6a and 7a from 1.5 g of the tritylated derivative of neamine 9, 1-iodohexane, without the addition of tetrabutylammonium iodide. The pure intermediate protected product 11c was obtained with a 50% yield, after passing through an alumina column using as eluent a cyclohexane/dichloromethane mixture of between 75/25 and 50/50 (MALDI MS, DHB, m/z=1567 [M+Na]$^+$). After deprotection in an acid medium as described earlier, the product 7c was isolated by simple water/dichloromethane extraction and washed in ethyl ether with a 66% yield. NMR $^1$H (400 MHz, MeOD) δ ppm=5.80 (d, J=3.6 Hz, 1H, H-1'), 4.12 (ddd, J=2.4 and 9.2 Hz, 1H, H-5'), 3.96 (ddd, J=7.2 Hz, 1H of 1CH$_2$O), 3.54-3.89 (m, 8H, H-4, H-3', H-5, 5H of 3CH$_2$O), 3.11-3.39 (m, 7H, H-1, H-6, H-4', H-3, H-2', H-6'b), 2.38 (ddd, 1H, J=4.0 and 12.0 Hz, H-2 eq.), 1.87 (ddd, J=12.0 Hz, 1H, H-2 ax.), 1.55-1.75 (m, 6H, 3CH$_2$), 1.25-1.47 (m, 18H, 9CH$_2$), 0.90-0.96 (m, 9H, 3CH$_3$); NMR $^{13}$C (100 MHz, MeOD) δ ppm=95.8 (C-1'), 81.1 (C-6), 79.6 (C-4 and C-4'), 77.2 (C-3'), 76.1 (C-5), 73.5, 73.3 and 73.0 (3CH$_2$O), 69.5 (C-5'), 53.4 (C-2'), 49.5 (C-1), 48.6 (C-3), 40.1 (C-6'), 31.5 (3CH$_2$), 29.9, 29.8 and 29.6 (C-2 and 3CH$_2$), 25.5, 25.4 and 25.2 (3CH$_2$), 22.3 (3CH$_2$), 13.0 (3CH$_3$); MS (MALDI, DHB) m/z=575 [M+H]$^+$.

3/Synthesis of the 3',4'-di-(naphthyl-2-methylene) neamine derivative 8a

This compound was obtained by deprotecting the derivative 11a in an acid medium.

The compound 11a was dissolved in a dichloromethane-trifluoroacetic acid mixture (v/v: 1/1) and anisole was added. After 24 hours reacting at room temperature, the solvents were evaporated under reduced pressure and water/diethylether extraction was performed. The subsequent purification was similar to that used for the other derivatives prepared from neamine.

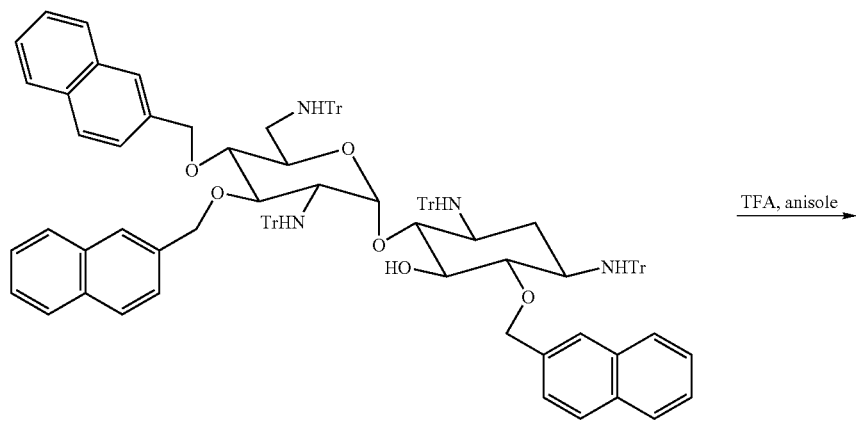

11a

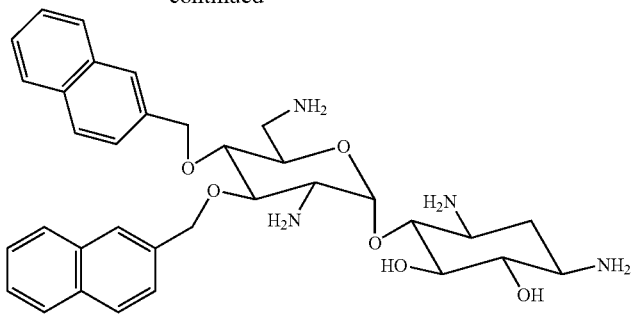

8a

Yield=10% (for 2 stages). NMR $^1$H (400 MHz, D$_2$O) δ ppm=7.10-7.90 (m, 14H, H-naphthyl), 5.87 (d, J=3.6 Hz, 1H, H-1'), 4.87 (d, J=12.0 Hz, 1H, CH$_2$-naphthyl), 4.78 (d, J=12.0 Hz, 1H, CH$_2$-naphthyl), 4.62 (d, J=12.0 Hz, 1H, CH$_2$-naphthyl), 4.59 (d, J=12.0 Hz, 1H, CH$_2$-naphthyl), 4.05-4.20 (m, 2H, H-3', H-5'), 3.88 (dd, J=10.0 Hz, 1H, H-4), 3.62 (dd, J=9.6 Hz, 1H, H-5), 3.54-3.61 (m, 2H, H-4', H-2'), 3.40-3.51 (m, 2H, H-6, H-3), 3.19-3.29 (m, 2H, H-6'b, H-1), 3.13 (dd, J=8.8 and 13.6 Hz, 1H, H-6'a), 2.42 (ddd, J=4.0 and 12.4 Hz, 1H, H-2 eq.), 1.79 (ddd, J=12.0 Hz, 1H, H-2 ax.); NMR $^{13}$C MHz, D$_2$O) δ ppm=132.7-134.4 (C-naphthyl), 125.3-128.4 (CH-naphthyl), 95.4 (C-1'), 78.2 (C-4'), 77.7 (C-4), 75.7 (C-3'), 75.1 (C-5), 74.9 (CH$_2$-naphthyl), 72.3 (C-6), 69.7 (C-5'), 52.6 (C-2'), 49.6 (C-1), 48.4 (C-3), 39.8 (C-6'), 28.2 (C-2); MS (ESI$^+$) m/z=603 [M+H]$^+$, 463, 441, 301, 141.

4/Synthesis of the tetratritylated 6-(naphthyl-2-methylene) neamine derivative 18a

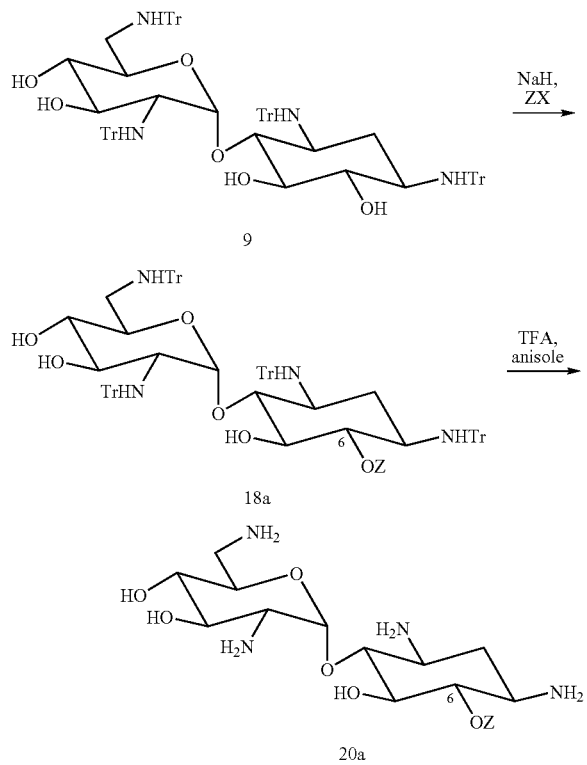

a: Z- = naphthyl-2-methylene

The tritylated derivative of neamine 9 (502 mg) was dissolved in a DMF/THF mixture (3 ml/3 ml) at room temperature under argon then NaH (170 mg; 10 eq.) was added. After 30 min. the 2-(bromomethyl)naphthalene (130 mg; 1.5 eq.) was added to the reaction mixture which was stirred at room temperature for 4 hours before being concentrated by evaporation under reduced pressure. The residue was dissolved in dichloromethane and washed with a saturated solution of ammonium chloride, water then brine. The organic phase was dried on magnesium sulphate, filtered then evaporated to dryness. The crude product was then purified on an alumina column with as eluent: CH$_2$Cl$_2$/MeOH (100/0 then 99.8/0.2) to give the derivative 18a (neamine tritylated and alkylated in the 6 position) with a yield of 12% (there remained a quantity essentially of starting compound 9 which had not reacted and which was recovered): MS (MALDI, DHB) m/z=1454 [M+Na]$^+$, 1430 [M+H]$^+$, 1211 [M−Tr+Na]$^+$, 1187 [M−Tr+H]$^+$. The tritylated groups can be eliminated for characterisation by treatment with trifluoroacetic acid according to the method described for the other neamine derivatives.

Compound 20a: Yield=82%; NMR $^1$H (400 MHz, D$_2$O) δ ppm=7.86-7.91 (m, 2H, H-naphthyl), 7.48-7.53 (m, 2H, H-naphthyl), 5.89 (d, J=3.6 Hz, 1H, H-1'), 5.04 (d, J=11.2 Hz, 1H, CH$_2$-naphthyl), 4.88 (d, J=11.2 Hz, 1H, CH$_2$-naphthyl), 3.88-3.98 (m, 3H, 1'-3', H-5', H-4), 3.85 (dd, J=8.8 and 9.2 Hz, 1H, H-5), 3.30-3.49 (m, 5H, H-3, H-4', H-2', H-6'b, H-1), 3.22 (dd, J=6.8 and 13.6 Hz, 1H, H-6'a), 2.42 (ddd, J=4.0 and 12.4 Hz, 1H, H-2 eq.), 1.83 (ddd, J=12.4 Hz, 1H, H-2 ax.); NMR $^{13}$C (100 MHz, D$_2$O) δ ppm=134.4 and 132.9 (C-naphthyl), 128.6, 128.0, 127.8, 127.6, 126.9 and 126.4 (CH-naphthyl), 96.0 (C-1'), 79.9 (C-6), 77.5 (C-4), 75.8 (C-5), 75.2 (CH$_2$-naphthyl), 70.6 (C-4'), 69.3 (C-5'), 68.2 (C-3'), 53.5 (C-2'), 48.9 (C-1), 48.4 (C-3), 40.1 (C-6'), 28.2 (C-2); MS (FAB$^+$, NBA): m/z=463 [M+H]$^+$, 303, 161, 141; HRSM (ESI$^+$): [M+H]$^+$ m/z theoretical=463.2557, found=463.2545.

This monoalkylated derivative 20a is not of interest as such but the synthesis of its tritylated derivative 18a, given as an example, forms the first stage of pathways B and C set out above.

B/ Biphasic Process in the Presence of a Phase Transfer Catalyst:

1/ Synthesis of the tetra-N-trityl 3'-O-para-methoxybenzyl derivative of neamine

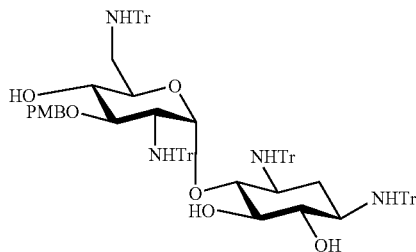

1 g of tetra-N-tritylated neamine 9 (1 eq, 0.775 mmol) was dissolved in 30 mL of toluene to which were successively added 430 mg (1.5 eq) tetrabutylammonium iodide and 0.15 mL of p-methoxybenzyl chloride (PMBCl, 1.2 eq). 15 mL of sodium hydroxide (50% m/m aqueous NaOH) were added to the solution, the two phases thus obtained were vigorously stirred to give an emulsion which was yellowish in colour. Two additions of 0.05 mL of PMBCl (0.4 eq) were made after 24 and 72 h. After 4 days, stirring was stopped and the reaction medium decanted, in order to eliminate the sodium hydroxide. The organic phase was diluted with ethyl acetate, washed with a saturated ammonium chloride solution and dried on anhydrous magnesium sulphate. The solvent was eliminated by evaporation under reduced pressure. The structure was confirmed by deriving the majority compound by reaction in DMF with sodium hydride and excess iodomethane. The protecting groups were eliminated in dichloromethane by the action of trifluoroacetic acid (TFA) and a few drops of anisole on the crude mixture previously obtained.

NMR $^1$H (MeOD, ppm, 400 MHz): 5.68 (s, H-1); 4.10 (m, H-5'); 4.02 (t, J=9.4 Hz, H-4), 3.95 (t, J=7.6 Hz, H-3'); 3.73 (t, J=9.4 Hz, H-6); 3.69-3.29 (m, H-2', H-5, H-3, H-6', H-4', H-6', H-1); 3.66; 3.60; 3.54 (3 s, H—OMe); 2.48 (m, H-2 eq) and 1.87 (m, H-2 ax).

NMR $^{13}$C (MeOD, ppm, 100 MHz): 164 (CO TFA); 117 (CF$_3$ TFA); 94.40 (C-1'); 84.99 (C-5); 79.50 (C-4'); 77.50 (C-3'); 76.23 (C-4); 73.40 (C-6); 71.51 (C-5'); 60.88; 60.84; 60.43 (3 C—OMe); 52.47 (C-2'); 50.70 (C-1); 49.63 (C-3); 40.30 (C-6') and 29.00 (C-2).

2/ Synthesis of the 4',6-di-O-[(2-naphthyl)methylene] derivative of neamine

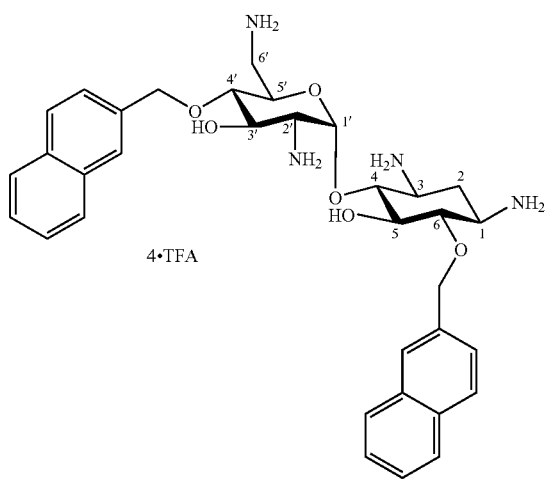

4·TFA 33 mg (3 eq, 0.83 mmol) of sodium hydride (60% suspension in oil) were added to a solution of 390 mg of neamine-tetra-N-Tr-3'-O-PMB (1 eq, 0.28 mmol) in 15 mL of DMF in an inert atmosphere. The reaction vessel was shaken and cooled in an ice bath. After 15 min, 152 mg (2.5 eq, 0.69 mmol) of 2-(bromomethyl)naphthalene were added; the bath was maintained at 0° C. for 30 min. then the reaction mixture was stirred at room temperature for 12 hours. The reaction was followed by TLC (toluene/ethyl acetate); 9/1). The reaction medium solvent was eliminated by evaporation under reduced pressure. The crude product thus obtained was dissolved in ethyl acetate then washed twice with distilled water and saturated NaCl solution. The aqueous phase was dried on anhydrous magnesium sulphate then concentrated under reduced pressure. The majority product was directly deprotected at 0° C. in 10 mL of dichloromethane by the action of 5 mL of TFA and a few drops of anisole. After 2 hours stirring, the TFA was eliminated by evaporation and co-evaporation under reduced pressure with ethanol then toluene. The derivative was then purified by chromatography on C$_{18}$ grafted silica gel (water 100% up to water/methanol 70/30), to give 40 mg of a translucent gum. Yield: 40%

NMR $^1$H (400 MHz, D$_2$O) δ ppm=7.90-7.50 (m, 14H, H-naphthyl); 6.01 (d, J=3.6 Hz, 1H, H-1'); 5.20 (m, 2H, CH$_2$-naphthyl); 4.90 (m, 2H, CH$_2$-naphthyl); 4.27 (dd, J=8 and 12 Hz, 1H, H:-3'); 4.18 (m, 1H, H-5'); 4.11 (dd, J=10 Hz, 1H, H-4); 3.91 (dd, J=10 Hz, 1H, H-5); 3.64 (dd, J=8 Hz, 1H, H-6); 3.28-3.46 (m, 5H, H-1, H-3, H-2', H-4', H-6'b); 2.98 (dd, J=8 and 12 Hz, 1H, H-6'a); 2.50 (m, 1H, H-2b); 2.08 (m, 1H, H-2a); NMR $^{13}$C (100 MHz, D$_2$O) δ ppm=132.0-135.0 (6C-naphthyl); 129.9-127.3 (14-CH-naphthyl); 97.2 (C-1'); 82.0 (C-6); 80.5 (C-4'); 79.5 (C-4); 78.0 (C-5); 76.4 (CH$_2$-naphthyl); 76.1 (CH$_2$-naphthyl); 70.6 (C-3'); 70.3 (C-5'); 55.6 (C-2'); 50.8 (C-1); 50.2 (C-3); 42.1 (C-6'); 30 (C-0); HRMS (ESI$^+$): [M+H:]$^+$ m/z calculated 603.3183, found 603.3199, [M+Na]$^+$ m/z calculated 625.3002, found 625.3005, [M+K]$^+$ m/z calculated 641.2741, found 641.2726.

3/ Synthesis of the tetra-N-trityl derivative of paromamine

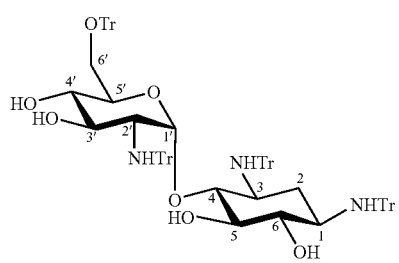

In a reaction vessel in an inert atmosphere, 2.5 g (1 eq, 5.78 mmol) of paromamine, 4HCl were put into suspension in 100 mL of anhydrous DMF and 5 mL of triethylamine (stored on potassium hydroxide). The solution was stirred and after 1 hr, 8 g (5 eq, 0.029 mol) previously dissolved in anhydrous DMF were added dropwise to the paromamine suspension. After 12 hours, approximately ten mg of 4,4'-N-dimethylaminopyridine were added to the reaction medium. After 24 h, the solvent was evaporated under reduced pressure. The residue obtained was dissolved in dichloromethane then washed twice with distilled water and saturated NaCl solution. The compound was purified by chromatography on triethylamine treated silica gel (cyclohexane/AcOEt) to obtain a white powder (3.32 g, 77%).

LRMS (MALDI, DHB) m/z=1331 [M+K]$^+$, 1315 [M+Na]$^+$, 1293 [M+H]$^+$

4/ Synthesis of the 3',6-di-O-[(2-naphthyl)methylene] derivative of paromamine 6a

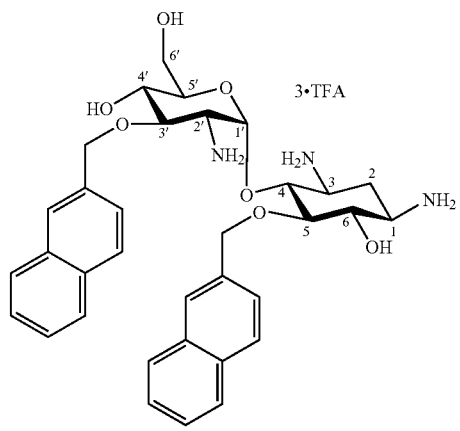

1 g (1 eq, 0.774 mmol) of N-tetratritylated paromamine was dissolved in 30 mL of toluene. 750 mg (3 eq, 2.32 mmol) of tetrabutylammonium bromide was added to the solution followed by 510 mg (3 eq, 2.32 mmol) of 2-(bromomethyl)naphthalene. 15 mL of a 50% (m/m) sodium hydroxide solution was added to the mixture. The two phases thus obtained were continually stirred to give an emulsion that becomes yellow with time. After 24 h the reaction medium was decanted, the sodium hydroxide was eliminated and then the organic phase was diluted with toluene. This was washed twice with distilled water then with an saturated aqueous NaCl solution, to be then dried on anhydrous magnesium sulphate. The solvent was eliminated by evaporation under reduced pressure to give a brownish residue. The required compound was then purified by chromatography on basic alumina via an elution gradient (cyclohexane/toluene; toluene/ethyl acetate) to give a yellowish powder (382 mg, 31.4%). 300 mg of N-tetratritylated 3',6-di-O-[(2-naphthyl)methylene]paromamine were deprotected at 0° C. in 10 mL of dichloromethane by the action of 5 mL of TFA and a few drops of anisole. After 2 hours stirring, the TFA was eliminated by evaporation under reduced pressure by co-distillation with ethanol then toluene. The derivative was then purified by chromatography on $C_{18}$ grafted silica gel (water 100% up to water/methanol 70/30), to give a translucent gum (62 mg, 30%).

NMR $^1$H (400 MHz, $D_2O$) δ ppm=7.85-7.55 (m, 14H, H-naphthyl); 5.65 (d, 1H, H-1'); 5.10 (m, 2H, $CH_2$-naphthyl); 4.95 (m, 2H, $CH_2$-naphthyl); 4.06 (dd, 1H, H-3'); 3.9 (m, 4H, H-4', H-5, H-5', H-6'$_a$); 3.75 (m, 3H, H-4', H-6, H-6'$_a$); 3.55 (m, 2H, H-3, H-2'); 3.40 (dd, 1H, H-1); 2.50 (m, 1H, H-2b); 1.85 (m, 1H, H-2a); NMR $^{13}$C (100 MHz, $D_2O$) δ ppm=167.8 and 164.4 (CO TFA); 136.3-134.5 (6CH-naphthyl); 130.29-128.0 (14-CH-naphthyl); 98.4 (C-1'); 82.0 (C-6); 82.2 (C-4); 81.2 (C-6); 78.1 (C-3'); 76.8 ($CH_2$-naphthyl); 76.7 ($CH_2$-naphthyl); 76.0 (C-5'); 71.43 (C-4'); 61.7 (C-6'); 54.5 (C-2'); 50.4 (C-3, C-1); 29.9 (C-2)

5/ Synthesis of the 3',6-di-O-[(1-naphthyl)methylene] Dderivative of neamine 6b

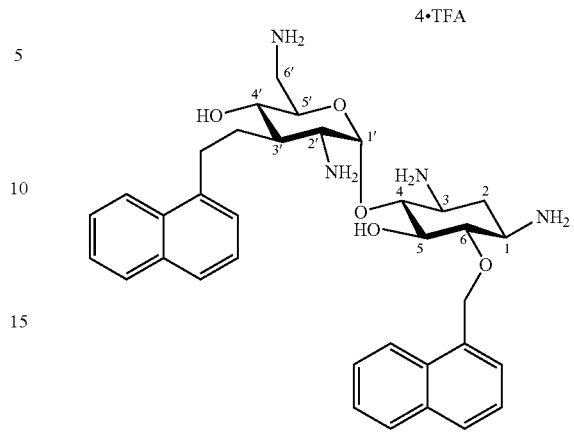

1 g of N-tetratritylated neamine 9 (1 eq, 0.775 mmol) was dissolved in 30 mL of toluene to which were successively added 428 mg (1.5 eq) tetrabutylammonium iodide and 350 µL (3 eq.) of 1-(chloromethyl)naphthalene. 15 mL of 50% (m/m) sodium hydroxide were added to the solution and the two phases thus obtained were vigorously stirred to give an emulsion which was yellowish in colour. The reaction was followed by TLC (toluene/ethyl acetate; 9/1). Three additions of 175 µL of 1-(chloromethyl)naphthalene (1.5 eq) were made after 12, 24 and 48 h. After 7 days, stirring was stopped and the reaction medium decanted, in order to eliminate the sodium hydroxide. The organic phase was diluted with toluene, washed with a saturated ammonium chloride solution and dried on anhydrous magnesium sulphate. The solvent was eliminated by evaporation under reduced pressure. The compound required was then purified by chromatography on alumina via an elution gradient (cyclohexane/toluene; toluene/ethyl acetate) to give a yellowish powder (500 mg, 41%). 300 mg of the isolated compound were deprotected at 0° C. in 10 mL of dichloromethane by the action of 5 mL of TFA and a few drops of anisole. After 2 hours stirring, the TFA was eliminated by evaporation and co-evaporation under reduced pressure with ethanol then toluene. The required derivative was then purified by chromatography on $C_6H_5$ grafted silica gel (water 100% up to water/methanol 70/30), to give a translucent gum (115 mg, 60.5%). LRMS (MALDI, DHB) m/z=641 [M+K]$^+$, 629 [M+Na]$^+$, 604 [M+H]$^+$.

6/ Synthesis of the tetra-N-tritylated 6-O-[(2-naphthyl)methylene] derivative of neamine

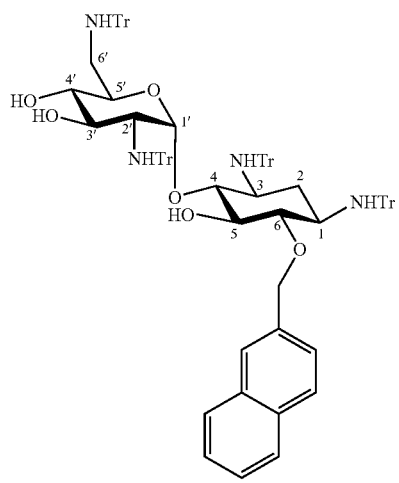

2 g of N-tetratritylated neamine 9 (1 eq, 1.55 mmol) were dissolved in 60 mL of toluene to which was successively added 486 mg (1.5 eq) hydrated tetrabutylammonium fluoride and 411 mg of 2-(bromomethyl)naphthalene (1.2 eq). 30 mL of 50% (m/m) sodium hydroxide were added to the solution and the two phases thus obtained were vigorously stirred to give an emulsion which was yellowish in colour. After 12 h of reaction, the reaction medium was decanted, the sodium hydroxide was eliminated and then the organic phase was diluted with toluene. This was washed twice with distilled water then with a saturated aqueous NaCl solution. The organic phase was then dried on anhydrous magnesium sulphate. After evaporation under reduced pressure, the compound required was purified by chromatography on alumina via an elution gradient (cyclohexane/toluene; toluene/ethyl acetate) to give a yellowish powder (450 mg, 18.5%). LRMS (MALDI, DHB) m/z=1454 [M+Na]$^+$, 1430 [M+H]$^+$, 1211 [M−Tr+Na]$^+$, 1187 [M−Tr+H]$^+$.

7/ Synthesis of the tetra-N-trityl 6-O-PMB derivative of neamine

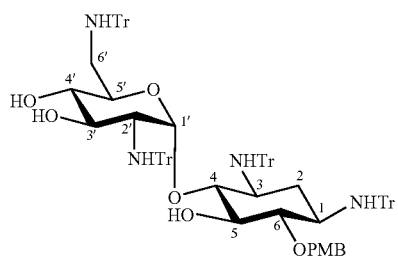

1 g of N-tritylated neamine 9 (1 eq, 0.775 mmol) was dissolved in 30 mL of toluene to which were successively added 243 mg (1 eq) tetrabutylammonium fluoride and 0.31 μL (2.5 eq) of PMBCl. 15 mL of 50% (m/m) sodium hydroxide were added to the solution and the two phases thus obtained were vigorously stirred to give an emulsion which was yellowish in colour. After 2 h stirring was stopped and the reaction medium decanted, in order to eliminate the sodium hydroxide. The organic phase was diluted with ethyl acetate, washed with a saturated aqueous ammonium chloride solution and dried on anhydrous magnesium sulphate. The solvent was eliminated by evaporation under reduced pressure. The structure was confirmed by deriving the majority compound by reaction in DMF with sodium hydride (60% in oil) and excess iodomethane. Deprotection was carried out in dichloromethane by the action of TFA and a few drops of anisole on the residue from evaporation previously obtained.

NMR $^1$H (MeOD, ppm, 100 MHz): 5.68 (s, H-1); 4.10 (m, H-5'); 4.02 (t, J=9.4 Hz, H-4); 3.95 (t, J=7.6 Hz, H-3'); 3.73 (t, J=9.4 Hz, H-6); 3.69-3.29 (massive, H-2', 5, 3, 6', 4', 6', 1); 3.66; 3.60; 3.54 (3 s, H—OMe); 2.48 (m, H-2 eq) and 1.87 (m, H-2 ax).

NMR $^{13}$C (MeOD, ppm, 100 MHz): 164 (CO TFA); 117 (CF$_3$ TFA); 94.40 (C-1'); 84.99 (C-5); 79.50 (C-4'); 77.50 (C-3'); 76.23 (C-4); 73.40 (C-6); 71.51 (C-5'); 60.88; 60.84; 60.43 (3 C—OMe); 52.47 (C-2'); 50.70 (C-1); 49.63 (C-3); 40.30 (C-6') and 29.00 (C-2).

8/ Synthesis of the 3',4',5-tri-O-[(2-naphthyl)methylene] derivative of neamine

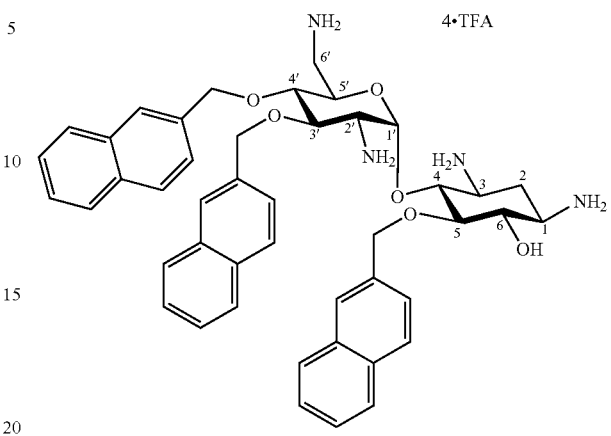

172 mg (10 eq, 4.3 mmol) of sodium hydride (60% suspension in oil) were added to a solution of 600 mg of tetra-N-tritylated 6'-O-PMB neamine (1 eq, 0.43 mmol) in 15 mL of anhydrous DMF in an inert atmosphere. The reaction vessel was shaken and cooled in an ice bath. After 15 min, 569 mg (6 eq, 2.58 mmol) of 2-(bromomethyl)naphthalene (previously dissolved in 5 mL anhydrous DMF) were added drop by drop; the bath was maintained at 0° C. for 30 min. then the reaction mixture was stirred at room temperature for 48 hours. The reaction was followed by TLC (100% toluene). The solvent was eliminated by evaporation under reduced pressure. The residue was dissolved in toluene then washed twice with distilled water and saturated aqueous NaCl solution. The aqueous phase was dried on anhydrous magnesium sulphate then concentrated under reduced pressure. The compound required was then purified by chromatography on basic alumina via a gradient (cyclohexane 100% to cyclohexane/toluene 40/60) to give a yellowish powder (300 mg, 38%). 300 mg of the isolated compound were deprotected at 0° C. in 10 mL of dichloromethane by the action of 5 mL of TFA and a few drops of anisole. After 2 hours stirring, the TFA was eliminated by evaporation under reduced pressure by generating an azeotrope with the ethanol then the toluene. The required derivative was then purified by chromatography on C18 grafted silica gel (water 100% up to water/methanol 70/30), to give a translucent gum (120 mg, 64.5%).

NMR $^1$H (400 MHz, D$_2$O) δ ppm=7.9-7.3 (m, 21H, H-naphthyl); 5.60 (d, 1H, H:-1'); 5.30 (m, 2H, CH$_2$-naphthyl); 5.0 (m, 2H, CH$_2$-naphthyl); 4.7 (m, 2H, CH$_2$-naphthyl); 4.55 (dd, 1H, H-3'); 4.25 (m, 1H, H-3'); 4.10 (m, 1H, H-4); 3.65 (m, 2H, H-5, H-6); 3.5 (m, 4H; H-2', H-4', H-3, H-6'$_b$); 3.30 (dd, 1H, H-1); 3.00 (m, 1H, H-6'$_a$); 2.50 (m, 1H, H-2$_b$); 2.25 (m, 1H, H-2$_a$); NMR $^{13}$C (100 MHz, D$_2$O) δ ppm=163.6 and 164.4 (CO TFA); 137.1-134.6 (9CH-naphthyl); 129.6-126.6 (21CH-naphthyl); 93.5 (C-1'); 85.0 (C-5'); 79.8 (C-4); 77.1 (CH$_2$-naphthyl); 75.9 (C-3'); 74.8 (C-6); 74.5 (C-5); 74.2 (CH$_2$-naphthyl); 73.9 (C-4'); 73.7 (CH$_2$-naphthyl); 51.6-50.33 (C-3, C-1, C-2'); 39.7 (C-6'); 29.2 (C-2). LRMS (MALDI, DHB) m/z=782 [M+K]$^+$, 766 [M+Na]$^+$, 744 [M+H]$^+$.

II—Antibacterial Activity

1/ Molecules Tested:

The molecules were dissolved in water or DMSO at a concentration of 5 or 10 mg/mL, then the solutions were diluted if necessary. A volume of 200 μL of each of them was put onto a 96-well plate.

2/ Strains Tested:

The following strains were used in the test for antimicrobial activity:

①  *Escherichia coli* ATCC25922=Gram negative strain, sensitive.
②  *Staphylococcus aureus* ATCC25923=Gram+, sensitive clinical strain.
③  *Staphylococcus aureus* 1199B=Gram+, mutant clinical strain overexpressing a NorA efflux pump of the MFS family, resistant to fluoroquinolones, including ciprofloxacin.
④  *Staphylococcus aureus* RN4220/pUL5054=Gram+strain overexpressing the MrsA ABC transporter, containing the multicopy plasmid pUL5054 carrying the msr(A) gene: EryR.
⑤  *Staphylococcus aureus* APH2"-AAC6'=Gram+resistant strain of MRSA (methicillin resistant *Staphylococcus aureus*) type capable of enzymatic modification of aminoglycosides: enzymatic resistance through the action of aminoglycoside-6'-N-acetyltransferase/2"-O-phosphoryltransferase.
⑥  *Staphylococcus aureus* APH3'=Gram+resistant strain of MRSA (methicillin resistant *Staphylococcus aureus*) type capable of enzymatic modification of aminoglycosides: enzymatic resistance through the action of aminoglycoside-3'-O-phosphoryltransferase.
⑦  *Staphylococcus aureus* ANT4'=Gram+resistant strain of MRSA (methicillin resistant *Staphylococcus aureus*) type capable of enzymatic modification of aminoglycosides: enzymatic resistance through the action of aminoglycoside-4'-O-phosphoryltransferase.

3/ Microbiological Tests:

A—Validation of the Strains

Before being used, each strain was individually tested for its antibiotic resistance. This means that for each strain, the MIC (minimal inhibitory concentration) of one or more reference antibiotics was tested, to be sure of the phenotypic stability of the bacterium.

The following antibiotics were tested:
*Escherichia coli* ATCC25922 (strain ①): Ampicillin, kanamycin, tetracycline, ciprofloxacin.
*Staphylococcus aureus* ATCC25923 (strain ②): Ampicillin, kanamycin, tetracycline, ciprofloxacin.
*Staphylococcus aureus* 1199B (strain ③): Ciprofloxacin, norfloxacin, pefloxacin.
*Staphylococcus aureus* RN4220/pUL5054 (strain ④): Erythromycin.
*Staphylococcus aureus* APH2"-AAC6', APH3' and ANT4' (strains ⑤, ⑥ and ⑦): Kanamycin, tobramycin, amikacin, gentamicin.

In the first instance, the strains were taken from stock kept at −80° C., and transferred onto Petri dishes containing MH agar medium. These dishes were incubated overnight at 37° C., then either used on the next day or kept at 4° C. In this way a dish could be used over 2-3 weeks.

The day before the test, a preculture of 1 mL of MH medium was seeded from an agar dish, and incubated overnight at 37° C.

The next day, the tests were performed in 96-well plates, using the Biomek2000 robot (Beckman). The antibiotic solutions were diluted there by a factor of 2, times 2, and put into the wells in order to cover a wide range of concentrations, in which the expected value should be found. A volume of inoculum made from the previous day's preculture diluted to $1/100^{th}$ strength was then added to each well. Each well was repeated. A non-contaminated control (blank), composed only of the culture medium, and a growth control, composed of the inoculum and the culture medium without antibiotic, were also included.

The plate was incubated at 37° C. Bacterial proliferation was measured by reading the optical density at 620 nm ($OD_{620\ nm}$) after 17-18 hours incubation, and the values obtained were compared with those found in the literature. If the values corresponded (to the nearest dilution), the strain was said to be "validated".

B—Screening

These tests were also carried out using 96-well plates and the Biomek2000 robot (Beckman). Each test was performed twice. A test consisted of putting the molecule to be tested with the bacterial strain. The previous day's bacterial preculture was therefore diluted to $1/100^{th}$ strength, and the molecule at a final concentration of 100 µg/mL (value selected arbitrarily) was added to the inoculum. The plate was incubated at 37° C., and the kinetics of the bacterial proliferation were monitored over 24 hours, by measuring the $OD_{620\ nm}$ at 0, 1, 4, 7, and 24 hours. Each plate also included controls of growth, non-contamination and resistance/sensitivity to a reference antibiotic.

A score was attributed to each well:

Score 1000=The molecule has no effect on the bacterial proliferation compared with the growth control.

Score 100=After 24 hours incubation, the bacterial proliferation is less compared with the growth control: only about 10% of the control value.

Score 10=After 24 hours incubation, there is almost no bacterial proliferation compared with the growth control: less than 10% of the control value.

C—Determination of the MIC

The molecules with a screening score of 10 or 100 were selected to determine their MICs relative to the strains tested.

As for the validation of the strains, the solution of the molecule selected was diluted by a factor of 2, times 2, using the Biomek2000 robot in 96-well plates to cover a wide range of concentrations. To each of these wells was added a volume of inoculum made from the previous days preculture diluted to $1/100^{th}$ strength. Each well was repeated. Again, controls of non-contamination, growth and resistance/sensitivity to a reference antibiotic were included in the experiment. The plate was incubated at 37° C., and the kinetics of the bacterial proliferation were monitored over 24 hours, by measuring the $OD_{620\ nm}$ at 0, 1, 4, 7, and 24 hours.

The MIC was the lowest concentration found to be capable of inhibiting bacterial proliferation after 24 hours incubation. Having no previous idea of this value it was possible that it might not fall within the range of dilutions chosen. If this was the case the operation had to be repeated adjusting this range.

Results

The antibiotic effects were therefore measured in terms of the minimal concentrations inhibiting bacterial growth (MIC) on various Gram negative and Gram positive bacteria, resistant or otherwise.

1/ Concerning Gram (+) Bacteria:

The MIC results, expressed in micrograms/mL, against [different strains] are shown for a certain number of molecules in Table I below and are compared with those of neamine and neomycin:

TABLE I

Minimum inhibitory concentrations (MIC) in micrograms/mL of the prepared neamine derivatives, neomycin B and neamine on wild and resistant strains of *Staphylococci aureus*

| Aminoglycosides | MIC μg/mL, S. aureus strains | | | | | | | |
|---|---|---|---|---|---|---|---|---|
|  | ATCC 25923 | Resistance pump NorA | Resistance pump MsrA | Enzyme APH2"-AAC6' | Enzyme APH3' | Enzyme ANT4' | ATCC 33592 HA-MRSA | VRSA-VRS-2 |
| Neomycin B | 2 | 1 | 1 | 1 | >128 | 32 | >128 | 128 |
| Neamine | 32 | 32 | 16 | 16 | >128 | >128 | >128 | >128 |
| 3'-mono2NM | >128 | >128 | >128 | >128 | >128 | >128 | ND | ND |
| 4'-mono2NM | >128 | >128 | >128 | >128 | >128 | >128 | ND | ND |
| 5'-mono2NM | >128 | >128 | >128 | >128 | >128 | >128 | ND | ND |
| 6'-mono2NM | >128 | >128 | >128 | >128 | >128 | >128 | ND | ND |
| 3',4'-di2NM 8a | 8 | 8 | 8 | 8 | 4 | 8 | 8 | 4 |
| 3',4'-di2NM 6a | 4-8 | 8 | 8 | 8 | 4 | 8 | 16 | 8 |
| 4',5-di2NM | 64 | 128 | 128 | 128 | 32 | 128 | 64 | 64 |
| 4',6-di2NM | 32 | 32 | 32 | 32 | 16 | 16 | 64 | 32 |
| 3',4',6-tri2NM 7a | 4 | 4 | 4 | 4 | 2 | 4 | 2 | 8 |
| 3',6-di1NM 6b | 8 | 8 | 8 | 16 | 8 | 8 | 4 | 4 |
| 3',4',6-trihexyl 7c | 4 | 4 | 8 | 8 | 4 | 8 | ND | ND |

It can be seen that the difunctionalised and trifunctionalised derivatives show antibiotic effects of considerable interest, particularly on bacteria resistant to conventional aminoglycosides.

2/ Concerning Gram (−) Bacteria:

Similar measurements were made on various Gram (−) bacteria. The corresponding results are given in tables II and III below. The strains tested were provided by R. Vanhoof (*E. coli* PAZ505H8101 and L58058.1, *P. aeruginosa* ATCC 27853, Psa.F03, *A. lwoffi* A1.88-483), Y. Glupczynski (*C. amalonaticus* Ca06AB0010), J. C. Pechere (*P. aeruginosa* PA02, PA03), P. Plésiat (*P. aeruginosa* PA01, PA21, PA22), H. Schweizer (*P. aeruginosa* PA405, PA406).

TABLE 2

Minimum inhibitory concentrations of the neamine derivatives prepared, the aminiglycosides used and neamine on wild type strains of Gram (-) bacteria and strains resistant due to an enzymatic modification.

|  | A. lwoffi ATCC 17925 | A. lwoffi AL88-483 APH3'-VIA | P. aeruginosa ATCC 27853 | P. aeruginosa Psa.F03 AAC6'-IIa | K. pneumoniae ATCC 700603 | E. Coli ATCC 25922 | E. Coli PAZ505 H8101 AAC6'-BI | E. Coli L58058.1 ANT"-IA |
|---|---|---|---|---|---|---|---|---|
| Gentamicin | 0.5 | 4-8 | 1 | >128 | 8 | <0.5-1 | 1 | 64-128 |
| Amikacin | 0.5 | >128 | 2-4 | 4 | 0.5 | 4 | 32 | 2 |
| Tobramycin | 0.5 | 1 | <0.25 | 128 | 4 | 0.5 | 32 | 64 |
| Neomycin B | 0.5 | >128 | 64 | 128 | 16-32 | 2 | 4 | 32 |
| Neamine | 4 | >128 | >128 | >128 | 32-64 | 32 | >128 | 32 |
| 3',4'-di2NM 8a | 8 | >128 | 32 | >128 | >128 | 32 | 16 | 16 |
| 3',4'-di2NM 6a | 16 | >128 | 64 | 128 | 128->128 | 64 | 32 | 32 |
| 4',5-di2NM | 32 | >128 | 128 | >128 | >128 | 128 | 128 | 128 |
| 4',6-di2NM | 32 | >128 | >128 | >128 | >128 | 128 | 64 | 128 |
| 3',4',6-tri2NM 7a | 4 | >16 | 4-8 | 8 | 16 | 16 | 4-8 | 4 |
| 3',6-di1NM 6b | 8 | >16 | 4-8 | 16 | 16 | 16 | 4-8 | 4-8 |
| 3',4',6-trihexyl 7c | ND | 64 | 8-16 | 8-16 | 16 | 8 | 8 | 8 |

TABLE 3

Minimum inhibitory concentrations (MIC) of the neamine derivatives prepared, the aminoglycosides used and neamine on wild type (WT) *P. aeruginosa*, and strains resistant due to overexpression of efflux pumps

| | MIC μg/mL | | | | | | | |
|---|---|---|---|---|---|---|---|---|
| | *P. aeruginosa* strains | | | | | | | |
| Aminoglycosides | ATCC 27853 WT | PAO7 (PAO1) WT | PAO2 Surex MexCD | PAO3 Surex MexEF | PA21 (MutGr1) Surexp MexAB | PA22 (PT629) Surex MexXY | PA405 (PAO509.5) Surexp TriABC deleted for 4 pumps[a] | PA406 (PA01095#1) deleted for 5 pumps[b] |
| Gentamicin | 1 | 2 | 1 | 1 | 1 | 4 | <0.125 | <0.125 |
| Amikacin | 2-4 | 2-4 | 2 | 2-4 | 2 | 8-16 | 0.5 | 1 |
| Tobramycin | <0.25 | 0.5 | 0.5 | <0.25 | 0.5 | 1 | <0.25 | <0.25 |
| Neomycin B | 64-128 | 4 | 8 | 4 | 4 | 32 | 2 | 4 |
| Neamine | >128 | >128 | >128 | >128 | >128 | >128 | 128 | 128 |
| 3′,4′-di2NM 8a | 16-32 | 64 | 16 | 8 | 64 | >128 | 8 | 8 |
| 3′,4′-di2NM 6a | 128 | 128 | 32 | 4 | >128 | >128 | 4 | 4 |
| 4′,5-di2NM | >128 | >128 | >128 | >128 | >128 | >128 | 16 | 16 |
| 4′,6-di2NM | >128 | >128 | 128 | 16 | >128 | >128 | 32 | 16 |
| 3′,4′,6-tri2NM 7a | 4-8 | 8-16 | 4 | 4 | 4 | 4 | 4 | 4 |
| 3′,6-di1NM 6b | 4-8 | 8-16 | 64 | 64 | 8 | 8 | 4 | 4 |
| 3′,4′,6-trihexyl 7c | 8-16 | 8-16 | 16 | 8 | 16 | 16 | 2 | 2 |

[a]deleted for Mex AB, Mex CD, Mex EF, Mex XY; [b]deleted for Mex AB, Mex CD, Mex EF, Mex XY, TriABC.

The 3′,6-di1NM and 3′,4′,6-tri2NM (7) derivatives can be seen to be also active on resistant bacteria expressing an RNA methylation enzyme (r-methylase): *C. amalonaticus* 06AB0010 arm, *E. coli* 06AB003 arm, *E. aerogenes* 06AB008 arm (MIC=4-16 μg/mL). On the other hand, these bacteria are totally resistant to gentamicin, amikacin and tobramycin (MIC>128 μg/ml).

REFERENCES

D. Moazed, H. F. Noller. "Interaction of antibiotics with functional sites in 16S ribosomal RNA". Nature 1987, 327, 389-394.

E. Riguet, S. Tripathi, B. Chaubey, J. Désiré, V. N. Pandey, J.-L. Décout. "A peptide nucleic acid-neamine conjugate that targets and cleaves HIV-1 TAR RNA inhibits viral replication". J. Med. Chem. 2004, 47, 4806-4809.

E. Riguet, J. Désiré, C. Bailly, J.-L. Décout. "A Route For Preparing New Neamine Derivatives Targeting Hiv-1 Tar RNA". *Tetrahedron* 2004, 60, 8053-8064.

E. Riguet, J. Désiré, O. Boden, V. Ludwig, M. Göbel, C. Bailly, J. L. Décout. "Neamine dimers targeting the HIV-1 TAR RNA". *Bioorg. Med. Chem. Lett.* 2005, 15, 4651-4655.

The invention claimed is:

1. Compound with a formula:

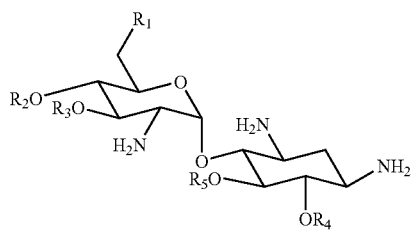

or a salt thereof, in which:
$R_1$=OH or $NH_2$;
$R_2$, $R_3$, $R_4$, and $R_5$, being identical or different, are H, an alkyl or haloalkyl group containing between 5 and 17 carbon atoms in a linear or branched chain, or an alkaryl group, wherein the aryl portion of the alkaryl group is naphthyl; and
if $R_5$=H, and
   if $R_2$=$R_3$=$R_4$, then $R_2$, $R_3$ and $R_4 \neq$H;
   if $R_2$=H, then $R_3 \neq$H and $R_4 \neq$H;
   if $R_3$=H, then $R_2 \neq$H and $R_4 \neq$H;
   if $R_4$=H, then $R_2 \neq$H and $R_3 \neq$H;
if $R_5 \neq$H then $R_2$ or $R_3$ or $R_4$=H, and
   if $R_2$=H, then $R_3 \neq$H and $R_4 \neq$H;
   if $R_3$=H, then $R_2 \neq$H and $R_4 \neq$H;
   if $R_4$=H, then $R_2 \neq$H and $R_3 \neq$H.

2. Compound according to claim 1 with a formula:

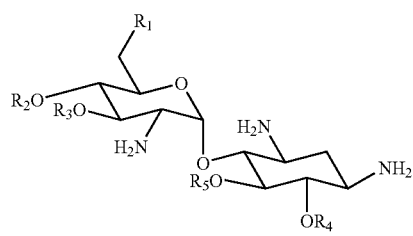

or a salt thereof, in which:
$R_1$=OH or $NH_2$;
$R_2$, $R_3$, and $R_4$, being identical or different, are H, an alkyl or haloalkyl group containing between 5 and 17 carbon atoms in a linear or branched chain, or an alkaryl group, wherein the aryl portion of the alkaryl group is naphthyl; and
if $R_2$=$R_3$=$R_4$, then $R_2$, $R_3$ and $R_4 \neq$H;

if $R_2$=H, then $R_3 \neq$H and $R_4 \neq$H;
if $R_3$=H, then $R_2 \neq$H and $R_4 \neq$H;
if $R_4$=H, then $R_2 \neq$H and $R_3 \neq$H.

3. Compound according to claim 1 characterised in that at least two of $R_2$, $R_3$, $R_4$, and $R_5$ are identical.

4. Compound according to any one of the previous claims characterised in that $R_2$ and/or $R_3$, and/or $R_4$ and/or $R_5$ are chosen from the following group: naphthyl-2-methylene, naphthyl-1-methylene and hexyl.

5. Compound according to claim 1 characterised in that its formula is selected from the following group: 3',6-O,O'-di(naphthyl-2-methylene)neamine; 3',4',6-O,O',O"-tri(naphthyl-2-methylene)neamine; 3',6-O,O'-di(naphthyl-1-methylene)neamine; 3',4',6-O,O',O"-tri-n-hexyl neamine; 3',4'-O,O'-di-(naphthyl-2-methylene)neamine; 3',6-O,O'di(naphthyl-2-propyl)neamine; 3',4',6-O,O',O"-tri(naphthyl-2-propyl)neamine; 3',6-O,O'-di(naphthyl-2-butyl)neamine and 3',4',6-O,O',O"-tri(naphthyl-2-butyl)neamine.

6. A pharmaceutical composition comprising a compound according to claim 1, or a pharmaceutically acceptable salt thereof, and possibly at least one other antibiotic.

7. A process of treating a bacterial infection, the process comprising the step of:
administering to a subject in need thereof an effective amount of a compound according to claim 1, or a pharmaceutically acceptable salt thereof.

8. The process according to claim 7, characterised in that the bacterial infection is caused by Gram positive bacteria or Gram negative bacteria.

9. A process for preparing compounds according to claim 1 comprising the following stages:
protection of alcohol and/or amine functional groups in the 1, 3, 2' and 6' positions on the paromamine or neamine molecules;
modification of the hydroxyl functional group in the 6 and/or 3' positions;
deprotection of functional groups in the 1, 3, 2' and 6' positions.

10. The process according to claim 9 characterised in that it is a biphasic process occurring in the presence of a phase transfer catalyst.

11. The process according to claim 9 characterised in that the modification of the hydroxyl functional group in the 6 position is an alkylation reaction with a compound RX, R being defined as $R_2$, $R_3$ and $R_4$, and X being a halogen or a sulphonyl group.

12. The process according to claim 11 characterised in that the alkylation reaction with the compound RX also occurs to the hydroxyl functional group in the 3' position, and possibly in the 4' position.

13. The process according to claim 11 characterised in that the alkylation reaction with the compound RX in the 6 position is followed by an alkylation reaction with a compound R'X to the hydroxyl functional group in the 3' position, and possibly by an alkylation reaction with a compound R"X to the hydroxyl functional group in the 4' position, R" and R' being identical or different and being identical to or different from R and being defined as $R_2$, $R_3$ and $R_4$.

14. The process according to claim 11 characterised in that the alkylation reaction with the compound RX in the 6 position is followed by protection of the hydroxyl in the 3' position, then by an alkylation reaction with the compound R'X to the hydroxyl functional group in the 4' position, R' being identical to or different from R and being defined as $R_2$, $R_3$ and $R_4$.

15. The process according to claim 10 characterised in that the modification of the hydroxyl functional group in the 6 position includes protection of the hydroxyl functional group in the 6 position, followed by an alkylation reaction with the compound RX of the hydroxyl functional groups in the 3' and 4' positions, or an alkylation reaction with the compound RX of the hydroxyl functional group in the 3' position followed by a second alkylation step with R'X of the hydroxyl functional group in the 4' position, R and R' being defined as $R_2$, $R_3$ and $R_4$, X being a halogen or a sulphonyl group.

16. The process according to claim 12 characterised in that the deprotection stage occurs over several hours, in such a way as to eliminate the R group in the 6 position.

17. The pharmaceutical composition according to claim 6, characterised in that the other antibiotic is a β-lactam or fluoroquinolone.

18. The process according to claim 8, characterised in that the Gram positive bacteria are *Staphylococcus aureus* or the Gram negative bacteria are *Escherichia coli*.

19. The process according to claim 8, characterised in that the bacteria are resistant to aminoglycosides.

20. The process according to claim 9, characterised in that the stage of protection includes tritylation of the alcohol and/or amine functional groups in the 1, 3, 2' and 6' positions on the paromamine or neamine molecules.

21. The process according to claim 9, characterised in that the stage of deprotection includes detritylation of the functional groups in the 1, 3, 2' and 6' positions.

22. The preparation process according to claim 14, characterised in that the step of protection of the hydroxyl in the 3' position includes protecting the hydroxyl in the 3' position with a group Z, wherein the group Z is acid-labile and is introduced by reaction with a halogenated derivative, sulphonylated derivative, or silylated derivative.

23. The preparation process according to claim 15, characterised in that the step of protection of the hydroxyl functional group in the 6 position includes protecting the hydroxyl functional group in the 6 position with a group Z, wherein the group Z is acid-labile and is introduced by reaction with a halogenated derivative, sulphonylated derivative, or silylated derivative.

* * * * *

UNITED STATES PATENT AND TRADEMARK OFFICE
CERTIFICATE OF CORRECTION

PATENT NO. : 8,729,035 B2  
APPLICATION NO. : 12/735511  
DATED : May 20, 2014  
INVENTOR(S) : Jean-Luc Decout et al.

Page 1 of 1

It is certified that error appears in the above-identified patent and that said Letters Patent is hereby corrected as shown below:

*In the claims*

In claim 2, at column 46, lines 48-59, formula: 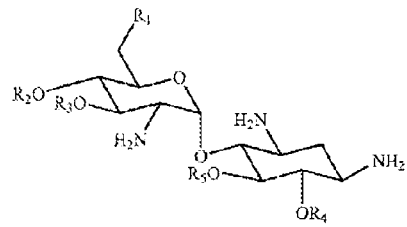 should be changed to the formula: 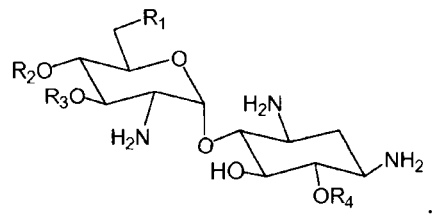 .

Signed and Sealed this  
Sixth Day of October, 2015

Michelle K. Lee  
*Director of the United States Patent and Trademark Office*